United States Patent [19]
Karimian et al.

[11] Patent Number: 5,675,006
[45] Date of Patent: Oct. 7, 1997

[54] METHODS OF MAKING UREAS AND GUANIDINES, INCLUDING, TERAZOSIN, PRAZOSIN, DOXAZOSIN, TIODAZOSIN, TRIMAZOSIN, QUINAZOSIN, AND BUNAZOSIN (EXEMPLARY OF 2-SUBSTITUTED QUINAZOLINE COMPOUNDS), AND MEOBENTINE, AND BETHANIDINE AND INTERMEDIATES THEREFOR

[75] Inventors: Khashayar Karimian; Keshava Murthy; Darren Hall, all of Brantford, Canada

[73] Assignee: Brantford Chemicals Inc., Brantford, Canada

[21] Appl. No.: 453,818

[22] Filed: May 30, 1995

Related U.S. Application Data

[62] Division of Ser. No. 4,114, Jan. 13, 1993, abandoned.

[30] Foreign Application Priority Data

Aug. 31, 1992 [CA] Canada ................... 2077252

[51] Int. Cl.$^6$ ................... C07D 403/00; C07D 403/02
[52] U.S. Cl. ................... 544/283; 544/284; 544/285; 544/286; 544/287; 544/288; 544/289; 544/290; 544/291; 544/292; 544/293; 514/259; 514/260
[58] Field of Search ................... 544/283–293

[56] References Cited

U.S. PATENT DOCUMENTS

| | | | |
|---|---|---|---|
| 3,511,836 | 5/1970 | Maxwell et al. | 514/259 |
| 3,949,089 | 4/1976 | Pfizer | 514/259 |
| 4,026,894 | 5/1977 | Winn et al. | 514/259 |
| 4,138,561 | 2/1979 | Crenshaw et al. | 514/259 |
| 4,251,532 | 2/1981 | Roteman | 514/259 |

FOREIGN PATENT DOCUMENTS

| | | |
|---|---|---|
| 1056831 | 6/1979 | Canada . |
| 1057754 | 7/1979 | Canada . |
| 1081229 | 7/1980 | Canada . |
| 1390015 | 4/1975 | European Pat. Off. . |
| 1464583 | 2/1977 | European Pat. Off. . |
| 2041932 | 9/1980 | European Pat. Off. . |
| 0034471 | 2/1981 | European Pat. Off. . |
| 0227450 | 7/1987 | European Pat. Off. . |
| 0227451 | 7/1987 | European Pat. Off. . |
| 2231571 | 11/1990 | European Pat. Off. . |
| 2350101 | 4/1975 | France . |
| 2321890 | 8/1975 | France . |
| 2457911 | 6/1975 | Germany . |
| 270068 | 9/1977 | Germany . |
| 2707058 | 9/1977 | Germany . |
| 2725019 | 12/1977 | Germany . |
| 181743 | 12/1992 | Hungary . |
| 1156973 | 8/1969 | United Kingdom . |
| 1390014 | 4/1975 | United Kingdom . |
| 1390015 | 4/1975 | United Kingdom . |
| 2021108 | 5/1979 | United Kingdom . |
| PCT/CA93/ 00355 | 8/1993 | WIPO . |

OTHER PUBLICATIONS

Synthetic Communications, vol. 18, No. 5, May 1988, U.S. pp. 525–530, A.V.N. Reddy, et al.: "An Efficient Synthesis of 3,4–dihydro–4–imino–2(1H)–quinazolines'".

Houben–Weyl: 'Methoden der Organischen Chemie', Band E4, 1983, pp. 352–364, published by Georg Thieme Verlag, Stuttgart, DE.

Houben–Weyl: 'Methoden der Organischen Chemie', Band E4, 1983, pp. 608–619, published by Georg Thieme Verlag, Stuttgart, DE.

Althius, T.H. and Hess, H.J., "Synthesis and Identification of the Major Metabolites of Prazosin Formed in Dog and Rat", *Journal of Medicinal Chemistry* vol. 20, p. 146 (1977).

Reiter, J. and Pongo, L., "On Triazoles. V[1,2], Synthesis of 1–and 2–$R^1$–3–$R^2$,$R^3$–Amino–5–amino–1,2,4–triazoles", *Journal of Heterocyclic Chemistry*, vol. 23, p. 401 (1986).

Curd, F.H.S., Landquist, J.K. and Rose, F.L., "Synthetic Antimalarials, Part XXXII. 2–p–Chloroanilino–4–β–diethylaminoethylaminoquinazolines containing Various Substituents in the Quinazoline Nucleus", *Journal of the Chemical Society*, p. 1759 (1948).

*Primary Examiner*—Matthew V. Grumbling
*Attorney, Agent, or Firm*—Ivor M. Hughes; Neil H. Hughes; Marcelo K. Sarkis

[57] ABSTRACT

Novel methods for the synthesis of substituted ureas and guanidines including Terazosin, Prazosin, Doxazosin, Tiodazosin, Trimazosin, Quinasin and Bunazosin (exemplary of 2-amino substituted Quinazolines), Meobentine and Bethanidine and novel intermediates suitable for use in such methods of synthesis are taught.

20 Claims, No Drawings

METHODS OF MAKING UREAS AND GUANIDINES, INCLUDING, TERAZOSIN, PRAZOSIN, DOXAZOSIN, TIODAZOSIN, TRIMAZOSIN, QUINAZOSIN, AND BUNAZOSIN (EXEMPLARY OF 2-SUBSTITUTED QUINAZOLINE COMPOUNDS), AND MEOBENTINE, AND BETHANIDINE AND INTERMEDIATES THEREFOR

This application is a divisional of application Ser. No. 08/004,114 filed Jan. 13, 1993 now abandoned.

FIELD OF INVENTION

This invention relates to novel processes of making ureas for example N-monosubstituted, N-N-disubstituted, N,N-N'-trisubstituted, N,N-N', N'-tetrasubstituted ureas and guanidines and derivatives thereof. A number of such compounds comprise 2-amino-substituted quinazolines (such as terazosin, prazosin, tiodazosin, bunazosin, quinazosin and trimazosin and doxazosin) and other guanidines (such as Meobentine and Bethanidine) which are known medicaments known to reduce blood pressure in hyperactive subjects.

This invention also relates to a number of novel intermediates (including novel ureas and novel guanidines) that may be used in the synthesis of for example the 2-amino-substituted quinazolines and guanidines and the methods of the synthesis thereof.

Some of these novel intermediates that are guanidines may also be useful as accelerators in the manufacture of rubber and as activators for thiazole accelerators.

BACKGROUND OF THE INVENTION

A number of medicines are guanidines. These guanidines include cyclized guanidines of the general formula 1.

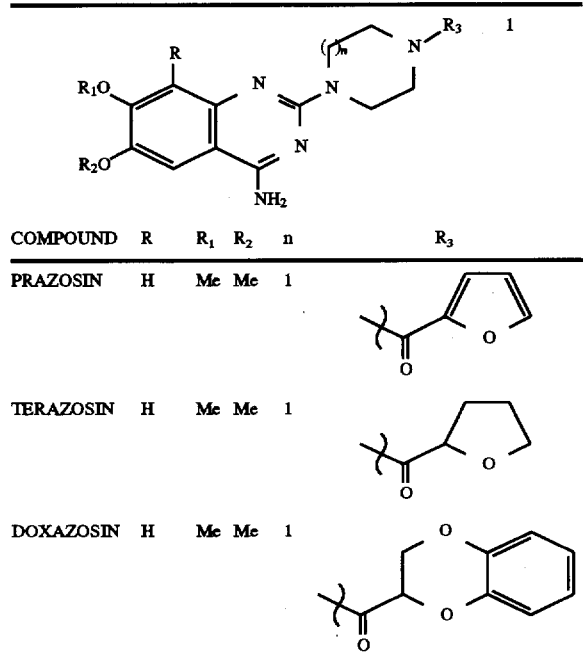

Thus they include the following cyclized guanidines of general formula 2.

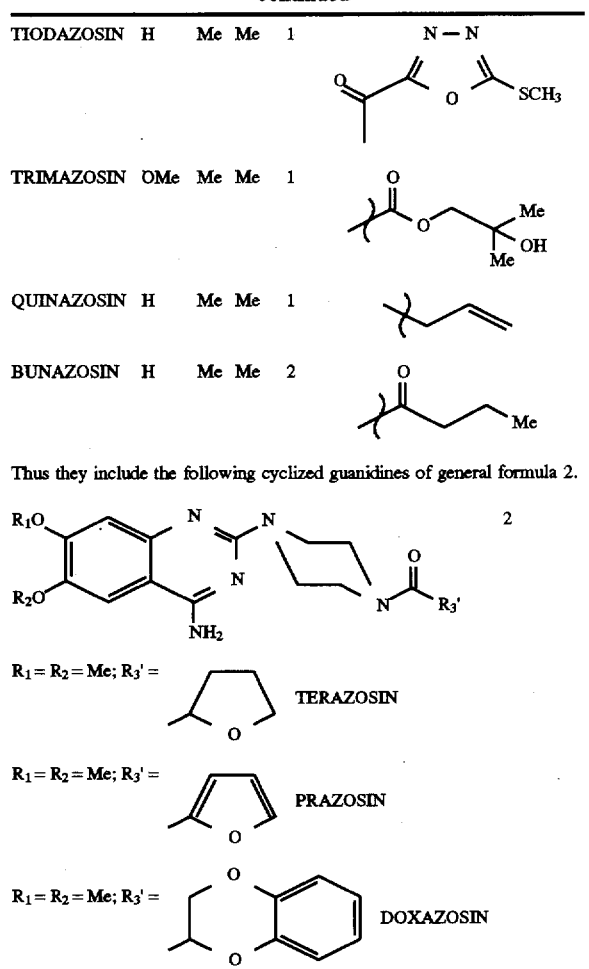

Thus they include the following cyclized guanidines of general formula 2.

The following compounds are exemplary:

1. PRAZOSIN

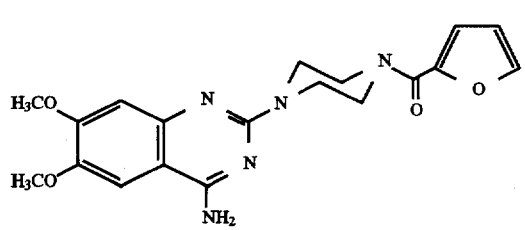

2. TERAZOSIN

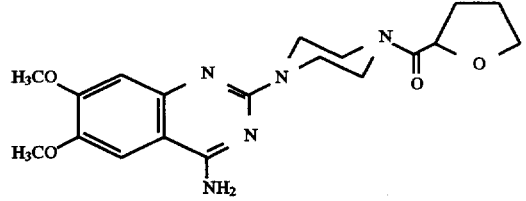

3. DOXAZOSIN

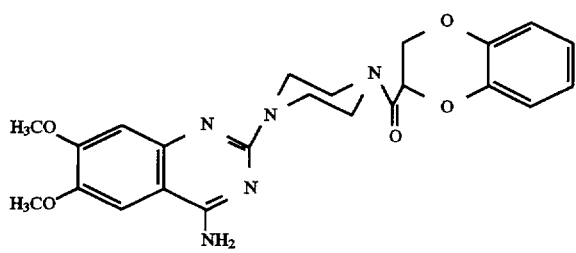

4. TRIMAZOSIN

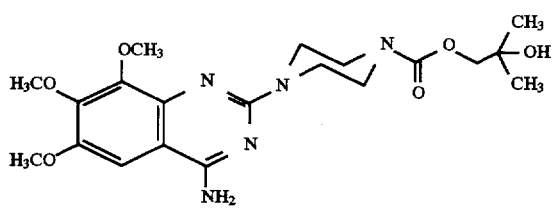

5. QUINAZOSIN

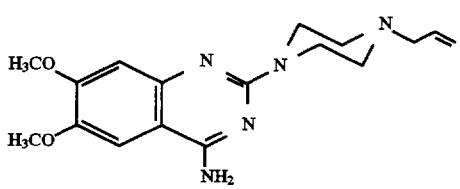

6. BUNAZOSIN

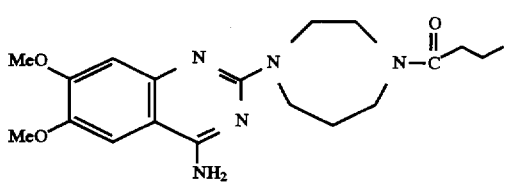

7. TIODAZOSIN

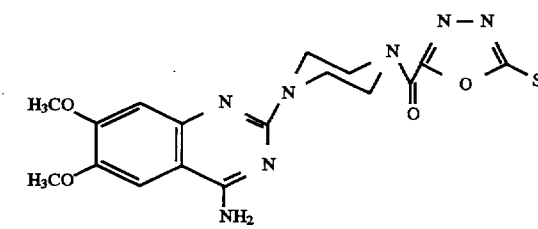

These guanidines also include uncyclized guanidines of the general formula 3.

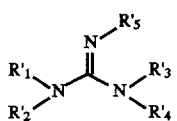

BETHANIDINE;

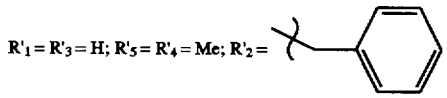

$R'_1 = R'_3 = H; R'_5 = R'_4 = Me; R'_2 =$

MEOBENTINE;

$R'_1 = R'_3 = H; R'_5 = R'_4 = Me; R'_2 =$ 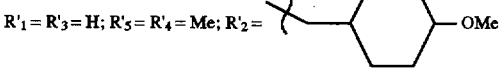

wherein Me is $CH_3$ (methyl).

The prior art preparations of cyclized and uncylized guanidines for example of Terazosin ($R_3$=tetrahydrofuryl), Prazosin ($R_3$=furyl), Doxazosin ($R_3$=1,4,-benzodioxan-2-yl), and Meobentine ($R'_1$=4-methoxybenzyl, $R'_2$=H, $R'_3$=methyl, $R'_4$=H, $R'_5$=$CH_3$) are discussed below.

Compounds of general formula 2 have been prepared by a number of approaches which may be classified into five general methods.

In method 1, a 4-amino-6,7-dimethoxy quinazoline that is substituted at C-2 position with a good leaving group X, is condensed with a proper amine. Up to nine steps are used to synthesize the 4-amino-6,7-dimethoxy quinazoline, starting from veratraldehyde [J. Chem. Soc. 1759, (1948) and J. Med. Chem. 20, 146, (1977)].

METHOD 1

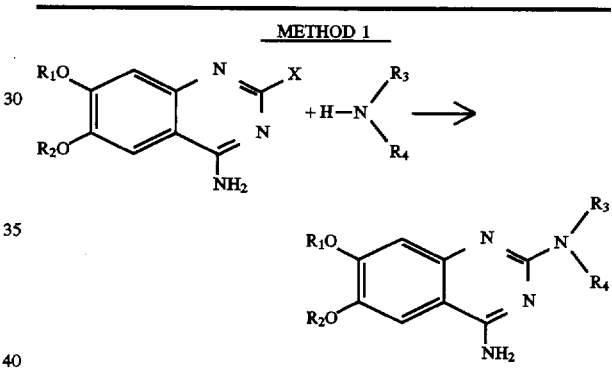

| X | Reference | |
|---|---|---|
| Cl | Fr. Pat. | 2321890 |
|  | Fr. Pat. | 2350101 |
|  | Can Pat. | 1057754 |
|  | Can Pat. | 1081229 |
|  | Ger Pat. | 2707068 |
|  | Ger Pat. | 2725019 |
|  | Eur Pat. | 0034471 |
|  | U.S. Pat. | 4251532 |
|  | U.S. Pat. | 4026894 |
|  | Brit Pat. | 1156973 |
|  | Brit Pat. | 2021108 |
| $SCH_3$ | Ger Pat. | 2707068 |
|  | Brit Pat. | 1156973 |
|  | Brit Pat. | 2021108 |
| $SO_2alkyl$ | Brit Pat. | 2021108 |

Those fine chemical manufacturers synthesizing prazosin, terazosin, and doxazosin for the most part use this process or a modification thereof. The major shortcoming of this method (method 1) is the low yields (between about 5 and 25%) which may be ascribed to the large number of steps involved.

In method 2, a 3,4-dimethoxyaniline that is substituted at the C-6 position with a nitrile, amide or amidine group is condensed with an amine that is N-substituted with an appropriate functional group, Y.

METHOD 2

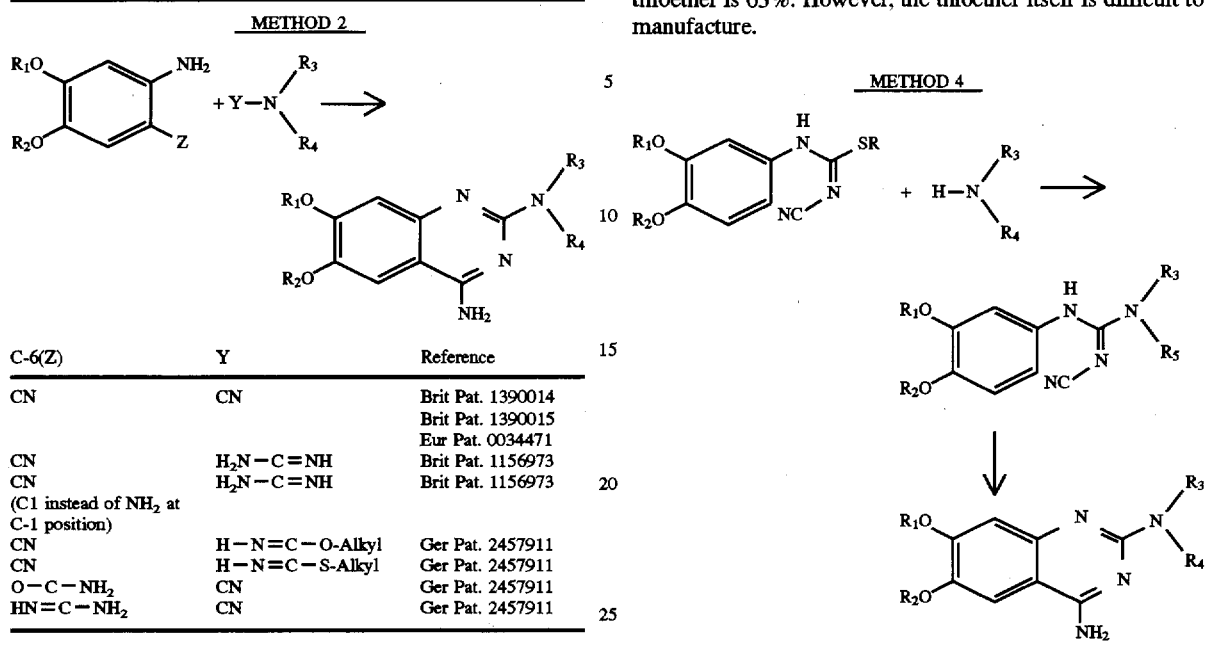

| C-6(Z) | Y | Reference |
|---|---|---|
| CN | CN | Brit Pat. 1390014 |
| | | Brit Pat. 1390015 |
| | | Eur Pat. 0034471 |
| CN | $H_2N-C=NH$ | Brit Pat. 1156973 |
| CN (Cl instead of $NH_2$ at C-1 position) | $H_2N-C=NH$ | Brit Pat. 1156973 |
| CN | $H-N=C-O$-Alkyl | Ger Pat. 2457911 |
| CN | $H-N=C-S$-Alkyl | Ger Pat. 2457911 |
| $O-C-NH_2$ | CN | Ger Pat. 2457911 |
| $HN=C-NH_2$ | CN | Ger Pat. 2457911 |

The processes taught by German Patent 2457911 propose the use of highly toxic cyanogen bromide. The yields of the processes are poor at best and thus not attractive for commercial production.

In method 3, 3,4-dimethoxy-6-cyanoaniline is converted to its corresponding isothiocyanate using thiophosgene. This is then condensed with a proper amine. The resulting thiourea is then S-alkylated (e.g. methyl iodide). High temperature reflux in the presence of ammonium chloride results in the insertion of the amine group, followed by ring closure to afford Terazosin (Bel. Pat. PCT/F18200034, Eur. Pat. 0034471). However thiophosgene is extremely toxic and its use is not practical on commercial scale due to high cost and limited availability.

Eur. Pat. 0034471). The reported yields starting from the thioether is 63%. However, the thioether itself is difficult to manufacture.

METHOD 4

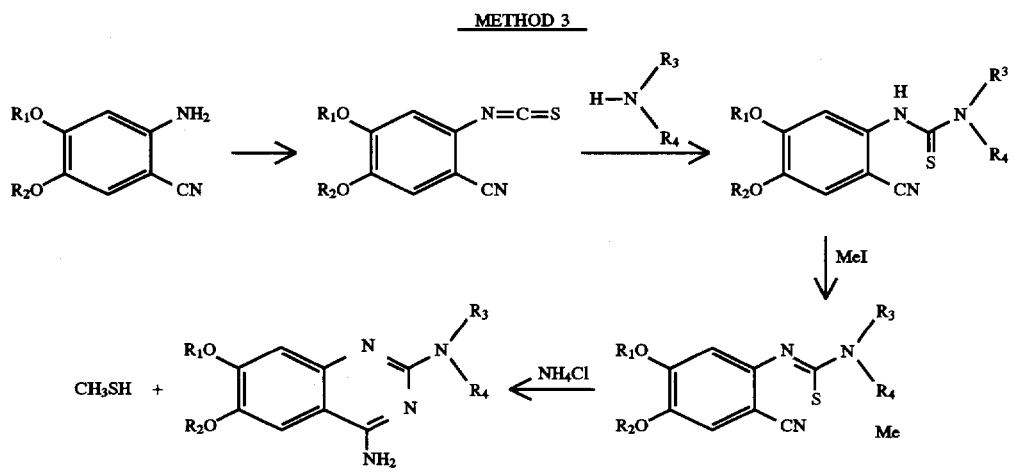

In method 5, 2-chloro-4-amionquinazoline is initially condensed with piperazine and the resulting amine is reacted with an acid chloride to afford the desired product (Brit. Pat. 1156973).

METHOD 3

In method 4, N-cyano-N-(3,4-dimethoxyphenyl)-5-methylisothiourea [see J. Heterocycl. Chem. 23, 401 (1986) or Hungarian Pat. 181743] is condensed with a proper amine to afford a carboxamidine which upon heating at high temperature affords the desired product (Can. Pat. 2015066,

METHOD 5

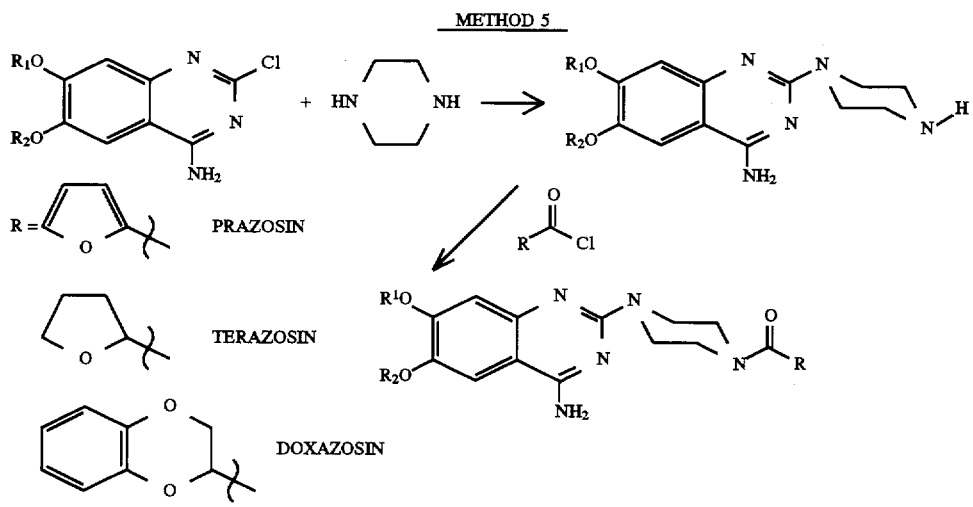

As in method 1, this process also fails to provide good yields, because of the number of steps involved in the preparation of the 2-chloroquinazoline starting material.

These methods suffer from various other shortcomings. For example, the use of 2-chloro-4-amino-6,7-dimethoxyquinazoline (method 1 and 5) is prohibitive due to the fact its synthesis involves nine steps from veratraldehyde and the overall yield is approximately 5-25% [F. H. S. Curd et. al., J. Chem. Soc. 1759 (1948) and J. Med. Chem. 20, 146 (1977)].

Activation of the amine group (method 2) requires the use of highly toxic cyanogen bromide (Y=CN), followed by further modification of the activating group (Y=H$_2$N—C=NH, HN=C—O—Alkyl). Use of ammonium thiocyanate, followed by alkylation of sulfur, will result in Y=HN=C—S—Alkyl. Nevertheless, the yields are generally low (ca. 40%). In method 3, although the reported yield of prazosin is high (ca. 68%), high toxicity and limited commercial availability of thiophosgene renders the method unattractive. In method 4, the overall yield starting from N-cyano N'-((3,4-dimethoxyphenyl)-S-methyl-isothiourea is reported to be ca. 63%. Nevertheless, the requirement of this isothiourea as starting material the preparation of which being very difficult and inefficient, renders the method unattractive.

Compounds of general formula 3 are synthesized using S-alkylated thiourea and the corresponding amine. The synthesis of Meobentine has been reported is U.S. Pat. No. 3,949,089 as described below:

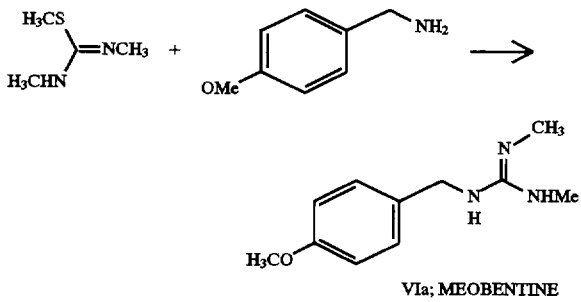

VIa; MEOBENTINE

The use of thiophosgene to manufacture thiourea is limited due to its high toxicity and commercial unavailability. Use of ammonium thiocyanate on the other hand followed by alkylation of the resulting thiourea generally affords low overall yields and therefore suffers from the same disadvantages described in the methods 2 and 3 (vide supra).

It is therefore an object of this invention to provide improved more efficient methods for the synthesis of compounds such as ureas and guanidines for example cyclized guanidines such as 2-amino substituted quinazolines of general formula 1 (e.g. Terazosin, Prazosin, Doxazosin, Tiodazosin, Trimazosin, Quinasin and Bunazosin) and for example uncyclized guanidines such as those of general formula 3 (e.g. Meobentine and bethanidine).

It is a further object of the invention to provide such improved more efficient processes which produce the desired compounds for example guanidines and ureas and in higher yields than in the prior art.

It is still a further object of the invention to provide such compounds for example quinazolines of very high purity (therefore having the desired efficacy).

It is still further object of this invention to provide (manufacture) novel intermediates including ureas and guanidines suitable for use to synthesize other guanidines for example 2-amino-substituted quinazolines including Terazosin, Prazosin, and Doxazosin and other guanidines for example meobentine and Bethanidine.

Further and other objects of the invention will be realized by those skilled in the art from the following summary of the invention and detailed description of the embodiments thereof.

SUMMARY OF THE INVENTION

According to one aspect of the invention a method of manufacture of compounds such as ureas and guanidines including cyclized guanidines for example 2-amino-substituted quinazolines compounds (for example Terazosin, Prazosin, Doxazosin, Tiodazosin, Trimazosin, Quinasin and Bunazosin) and for example uncylized guanidines such as meobentine and Bethanidine are provided, comprising:

(a) (i) adding oxygen or a hetero radical containing oxygen to an intermediate compound for example by adding a carbonyl (c) to an amine in one embodiment in a form of converting an amine to its corresponding urea or (ii) starting with an intermediate compound containing oxygen for example containing a carbonyl group in some embodiments connected to an amine or forming part of a urea, and (b) carrying out in any order (i) or (ii) of this subparagraph (b)

(i) react the oxygen for example the oxygen of a carbonyl, with a suitable electrophile (EP) in which the combination of the oxygen-electrophile (O—EP) becomes a good leaving group that can be and is subsequently displaced by for example a nucleophile (such as for example ammonia or an amine) and (ii) adding a desired radical to the results of subparagraph (a) or b (i) if step (i) of subparagraph (b) is carried out before this step (ii), and (c) optionally, and if required, closing a ring to form for example a 2-amino-substituted quinazoline.

Other guanidines including quinazolines may also be manufactured according to the invention as would be understood by persons skilled in the art.

According to another aspect of the invention the desired radical is ammonia or an amine radical.

In this way, greater yields and higher purity in the manufacture of known products can be achieved. Furthermore compounds of the invention may be conveniently prepared by a "one pot" synthesis.

EP is preferably $POCl_3$. EP may also comprise: $PCl_5$, $P_2O_5$, tosyl chloride ($CH_3\ SO_2\ Cl$)—TsCl— and in some instances mesyl chloride ($CH_3\ SO_2\ Cl$)—MsCl—.

Thus according to another aspect of the invention, such a method comprises;

a) taking a known intermediate and adding oxygen or a hetero radical containing oxygen to it for example by adding a carbonyl (c) to an amine;

b) adding a desired radical to the results of (a);

c) adding a suitable electrophile (EP) to react with the oxygen to yield a reaction product (O—EP) which is a leaving group susceptible to replacement by a nucleophile such as ammonia or an amine;

d) replacing the reaction product (leaving group) of (c) with $NH_2$ or an amine group;

e) closing a ring if required to produce a desired compound.

In accordance with another aspect of the invention, such a method may comprise;

f) taking an intermediate compound carrying oxygen (for example the results of subparagraph (a) of the previous paragraph) and adding a suitable electrophile (EP) to react with the intermediate at the site of the oxygen to yield a reaction product therebetween as a leaving group susceptible to replacement by a nucleophile such as ammonia or amine;

g) replacing the reaction product (O—EP) (leaving group) of (f) with $NH_3$ or ammonia group;

h) optionally adding a radical if desired before or after carrying out either or both of steps (f) and (g);

i) closing a ring if required to produce a desired compound.

According to another aspect of the invention a method of manufacture of substituted ureas and guanidines including 2-amino-substituted quinazoline compounds (for example Terazosin, Prazosin and Doxazosin) is provided comprising;

(a) converting an amine to its corresponding urea;

substituting the $NH_2$ group of the substituted urea of (a) by an amine;

(c) reacting the resulting substituted urea with a suitable electrophile (EP) to yield a reaction product in which the oxygen of the urea reacts with the electrophile (EP) to become a good leaving group that can be displaced by a nucleophile for example such as ammonia or an amine;

(d) replacing the reaction product between the oxygen and EP (leaving group) of (c) by $NH_3$ or an amine to provide for example unsymmetrically substituted guanidines;

(e) optionally, and if required closing the resulting substituted guanidine to provide 2-amino-substituted quinazolines such as Terazosin, Prazosin, and Doxazosin.

In this way, greater yields and high purity of known products can be achieved, for example steps (a) and (b) of the immediately previous process being both converted in very high yields of 85–95%. Furthermore compounds of the invention may be conveniently prepared by a "one pot" synthesis, starting from the substituted urea (b).

According to another aspect of the invention, such a method may comprise;

a) taking a known intermediate and converting it to a urea;

b) adding a suitable electrophile (EP) to react with the oxygen of the urea to yield a reaction product as a leaving group susceptible to replacement by an amine;

c) replacing the leaving group of (b) with an amine;

d) closing a ring if required to produce a desired compound.

In accordance with another aspect of the invention, such a method may comprise;

e) taking a known intermediate and converting it to a urea;

f) adding a suitable electrophile (EP) to react with the oxygen of the urea to yield a reaction product as a leaving group susceptible to replacement by an amine;

g) displacing the leaving group of the reaction product of (f) with an amine;

h) closing the ring if required to produce a desired compound.

The salts of the guanidines may also be produced for example Terazosin hydrochloride and terazosin hydrochloride dihydrate and Doxazosin Mesylate.

In accordance with another aspect of the invention, exemplary novel processes of the manufacture of guanidine compounds are disclosed. In one method, guanidine compounds are synthesized starting for example from 3,4-dimethoxyanthranilonitrile I and the corresponding amine III. The initial reactants are all available and are easily manufactured as would be understood by persons skilled in the art.

In an exemplary method, an amine I (nitrile) is converted to its corresponding urea II in high yields (85–90%) with sodium cyanate. The resulting urea is then condensed with a proper amine III [N-(tetrahydro-2-furoyl) piperazine in the case of Terazosin, N-(2-furoyl) piperazine in the case of Prazosin, N-(1,4-Benzodioxan-2-carbonyl) piperazine in the case of Doxazosin, Methylthiooxadiazale carbonyl piperazine in the case of Tiodazosin, 2,2-dimethyl-2-hydroxy ethyl ester piperazine in the case of Trimazosin, propene carbonyl piperazine in the case of Quinazosin and butyroyl diazo cycloheptane (a 7-membered dinitrogen radical) in the case of bunazosin] in refluxing pyridine to afford IV (85–95% yield). The intermediate IV is then reacted with an appropriate electrophile (e.g. $POCl_3$, $PCl_5$, tosyl chloride, phosphorous pentoxide), resulting in the conversion of the oxygen of the urea into a good leaving group (V). Addition of ammonia (e.g. ammonia gas or ammonium carbonate) will then displace the activated oxygen function, forming the corresponding guanidine VI. Quinazoline ring system VII is then formed by the attack of the amino group of the guanidine on the nitrile. This is a very facile reaction and in fact intermediate VI was not isolated.

The following reaction scheme thus presents itself:

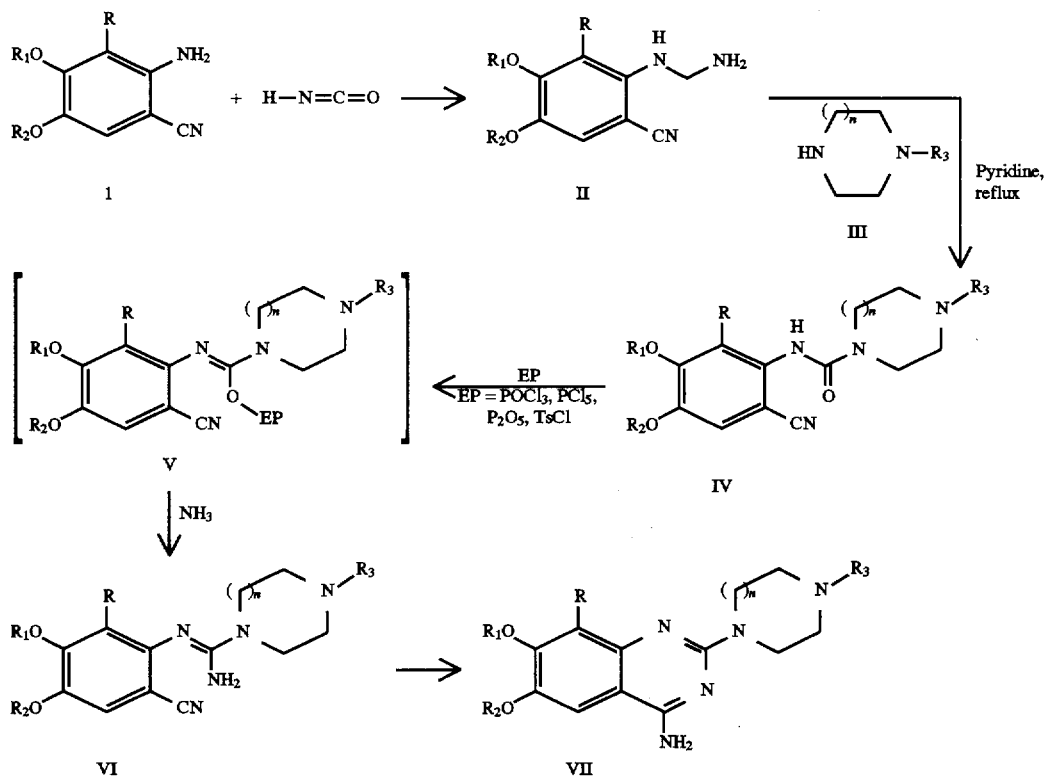

wherein —O—EP is the reaction of the urea oxygen and EP, and is a leaving group substitutable by —NH$_2$ or an amine.

In this scheme R may be hydrogen or lower alkoxy (for example methoxy), R$_1$ and R$_2$ may be lower alkyl (for example methyl), n is a number selected from 1 and 2 and R$_3$ may be selected from unsubstituted or substituted furoyl (for example furoyl or tetrahydrofuroyl), benzodioxanyl carbonyl (for example 1,4-benzodioxan-2-yl carbonyl), lower alkylthiooxadiazole carbonyl (for example methylthiooxadiazole carbonyl), dialkyl hydroxy alkyl ester (for example 2,2-dimethyl hydroxy ethyl ester), alkene (for example propene) and alkyroyl (for example butyroyl).

The following chart identifies combinations of substituents for identified Medicines:

| COMPOUND | R | R$_1$ | R$_2$ | n | R$_3$ |
|---|---|---|---|---|---|
| PRAZOSIN | H | Me | Me | 1 | furoyl |
| TERAZOSIN | H | Me | Me | 1 | tetrahydrofuroyl |

-continued

| COMPOUND | R | R$_1$ | R$_2$ | n | R$_3$ |
|---|---|---|---|---|---|
| DOXAZOSIN | H | Me | Me | 1 | benzodioxanyl carbonyl |
| TIODAZOSIN | H | Me | Me | 1 | methylthiooxadiazole carbonyl |
| TRIMAZOSIN | OMe | Me | Me | 1 | 2,2-dimethyl hydroxy ethyl ester |
| QUINAZOSIN | H | Me | Me | 1 | propene |
| BUNAZOSIN | H | Me | Me | 2 | butyroyl |

Thus the following is specifically included:

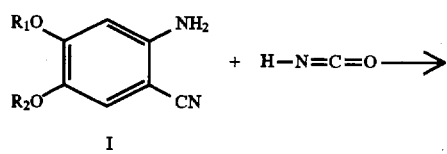

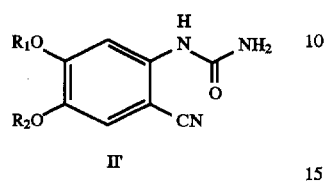

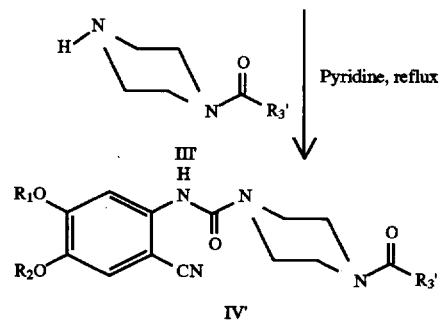

EP=POCl₃, PCl₅, P₂O₅, TsCl   EP

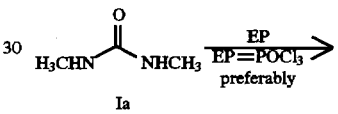

wherein —O—EP is the reaction of the
urea oxygen and EP, and is a leaving
group substitutable by —NH₂ or ammonia

NH₃

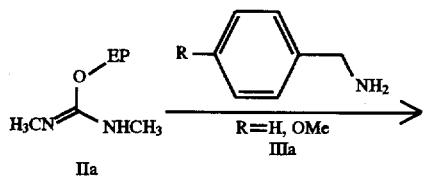

$R_3' =$ 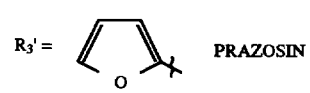 PRAZOSIN

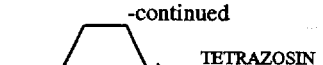 TETRAZOSIN

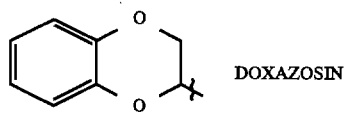 DOXAZOSIN

The radical $R_3'$ and $R_3'$-C may be substituted by other radicals as is apparent from examination of the substituents for $R_3'$.

Usual work up of the reaction mixture results in the isolation of the desired product. Compounds II (including II'), IV (including IV'), V (including V') and VI (including VI') are novel and the processes of their manufacture are also novel.

In the case of Meobentine and Bethanidine, urea Ia, for example, dimethyl urea, is reacted with Electrophile (EP) to produce (IIa). Condensation of benzylamine (IIIa) with IIa affords Meobentine and Bethanidine.

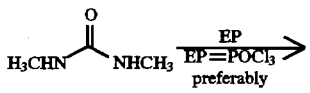

wherein —O—EP is the reaction of the urea oxygen and EP and is a leaving group substitutable by —NH₂ or ammonia

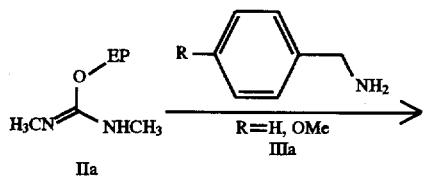

R=OMe; MEOBENTINE
R=H; BETHANIDINE

Compounds IIa are new and the processes of their manufacture are also novel.

In another method, for example the urea nitrile II is initially activated with an electrophile (EP) such as POCl₃, PCl₅, etc, (see above) to form intermediate VIII in which the oxygen function of the urea reacted with the EP becomes a good leaving group. Displacement of the oxygen by a proper amine III and subsequent work-up results in the isolation of the desired quinazoline VII (for example terazosin). Compounds II, VI and VIII are novel. Preferably EP is PCOl₃.

The following reaction scheme presents itself:

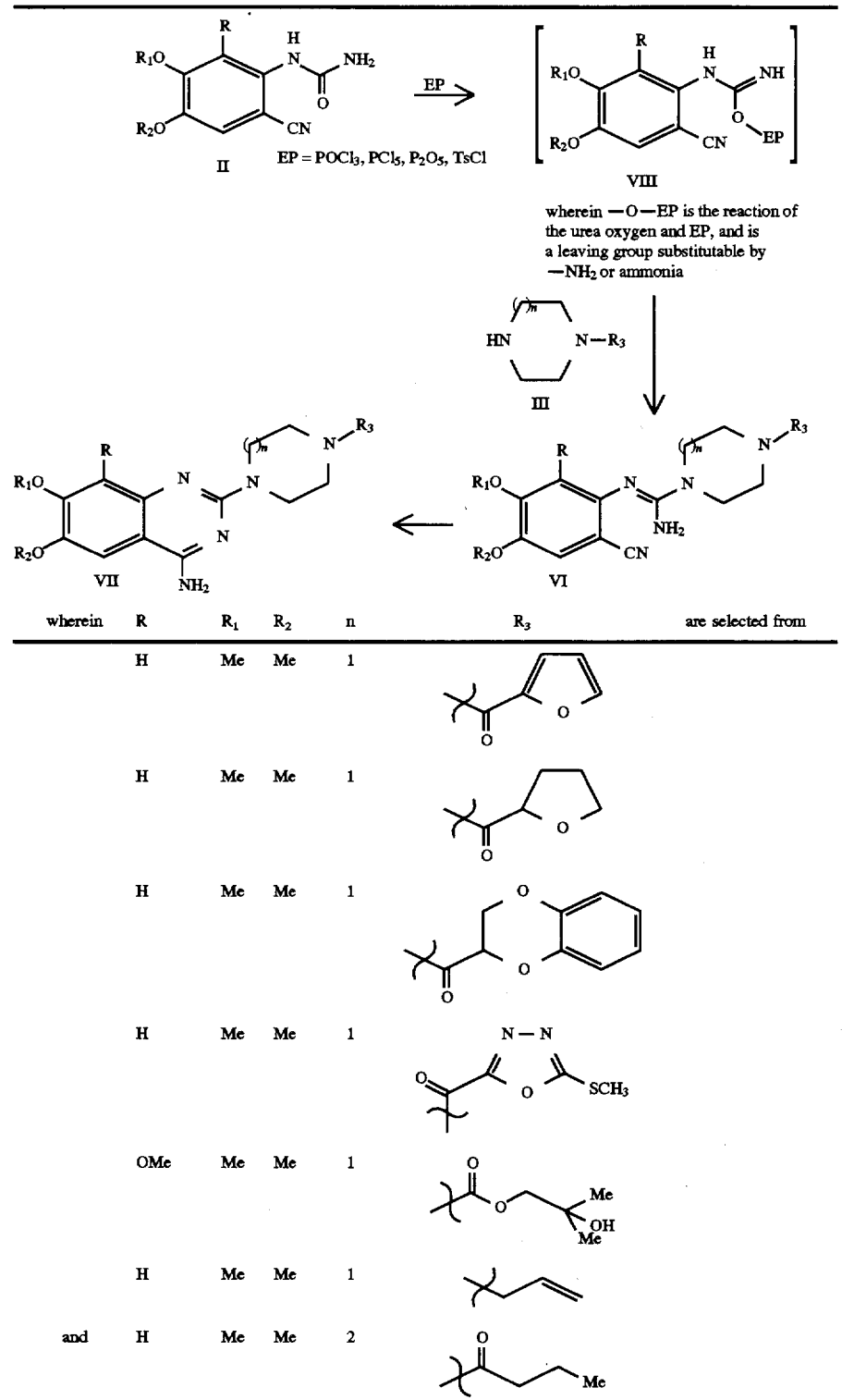

Thus the following is specifically included:

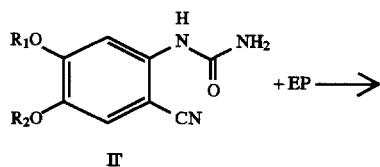

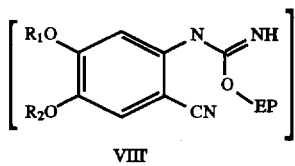

wherein —O—EP is the reaction of the urea oxygen and EP, and is a leaving group substitutable by —NH₂ or ammonia

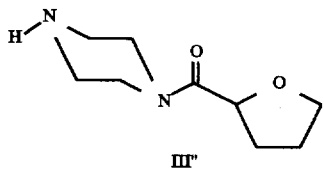

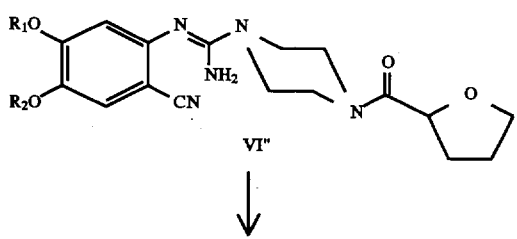

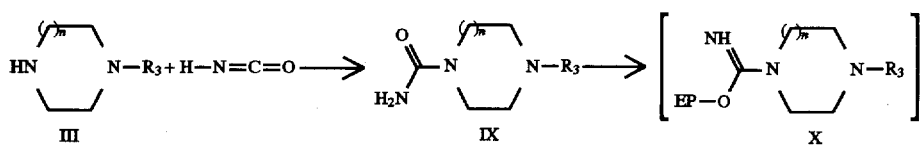

(The tetrahydrofuryl radical may be substituted by furyl or 1,4-benzodioxan-2-yl to produce Prazosin and Doxazosin, respectively. The tetrahydrofuryl radical, tetrahydrofuroyl radical, and tetrahydrofuroyl piperazine radical may also be substituted by the other radicals for example those for $R_3'$.)

In another method, for example the amine III is converted to its corresponding urea IX with cyanic acid. Again the oxygen function of the urea is converted to a good leaving group using an electrophile (EP) such as $POCl_3$, $PCl_5$, etc. to form X. Displacement of the activated oxygen by the amine function of I and subsequent work-up results in the isolation of the desired quinazoline VII, which may be converted to its pharmaceutically acceptable salts (for example the hydrochloride or mesylate salt). The following reaction scheme presents itself:

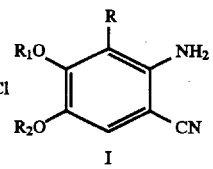

wherein —O—EP is the reaction of the urea oxygen and EP, and is a leaving group substitutable by —NH₂ or ammonia $EP = POCl_3, PCl_5, P_2O_5, MsCl, TsCl$

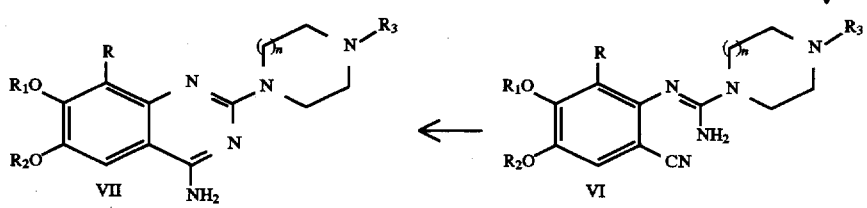

wherein    R    $R_1$    $R_2$    n    $R_3$    are selected from

-continued
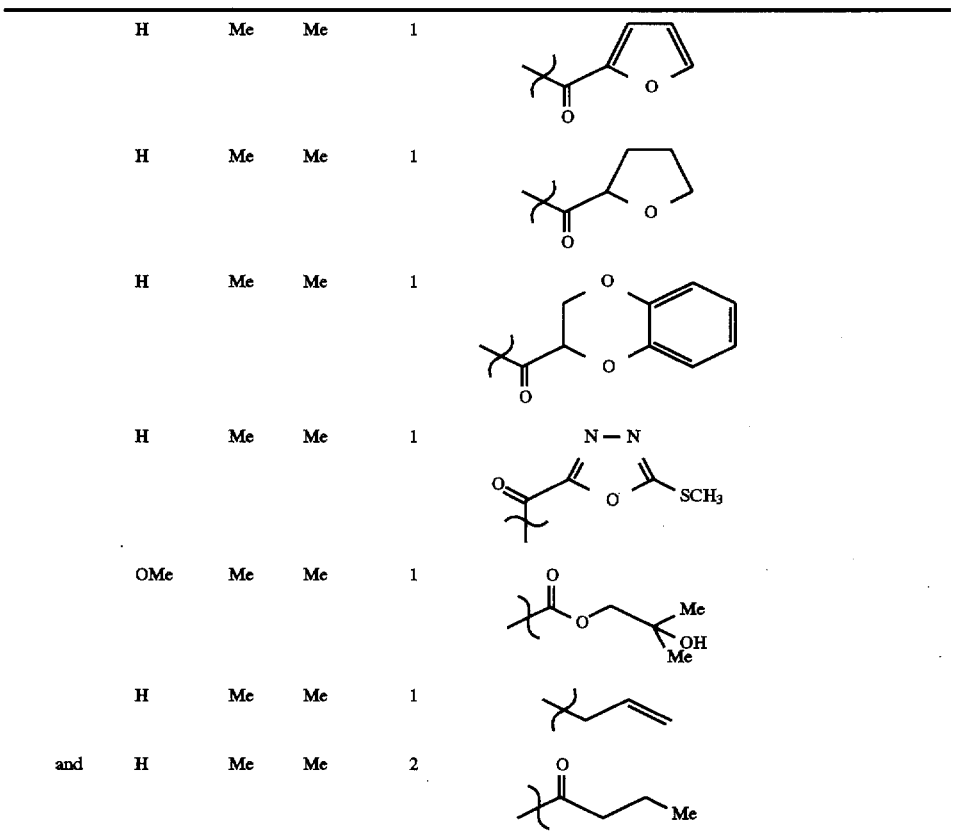
| | | | | |
|---|---|---|---|---|
| | H | Me | Me | 1 |
| | H | Me | Me | 1 |
| | H | Me | Me | 1 |
| | H | Me | Me | 1 |
| | OMe | Me | Me | 1 |
| | H | Me | Me | 1 |
| and | H | Me | Me | 2 |
Compounds IX, X and VI are novel and processes of their manufacture are also novel.
Thus the following is included:
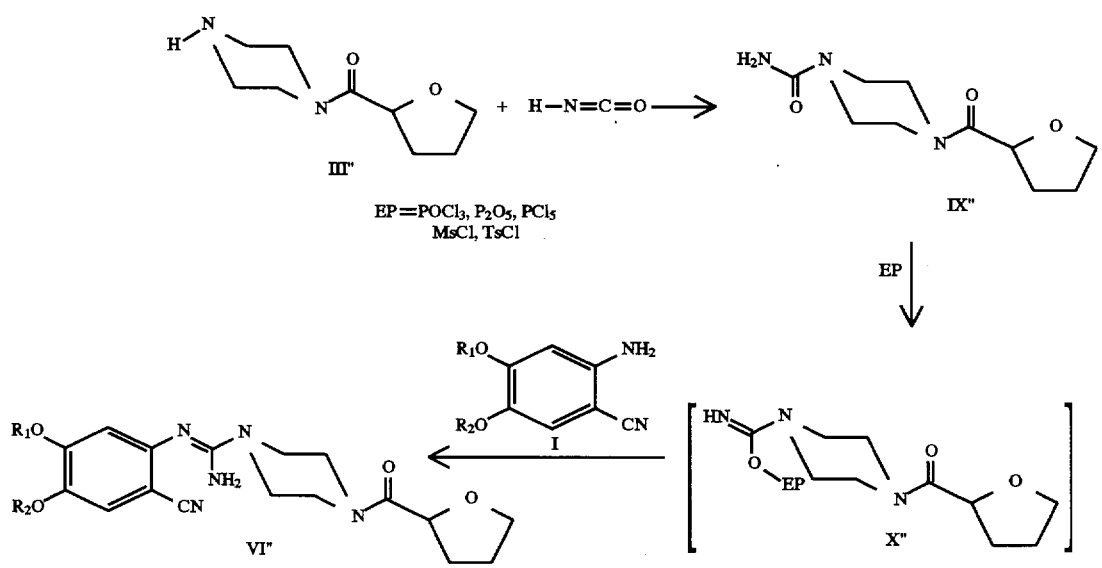
wherein —O—EP is the reaction of the urea oxygen and EP, and is a leaving group substitutable by —NH₂ or ammonia

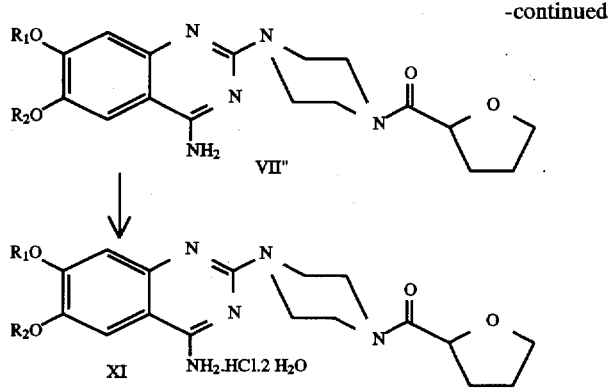

(Once again the tetrahydrofuryl radical may be replaced by furyl or 1,4-benzodioxan-2-yl). The tetrahydrofuryl radical and the tetrahydrofuroyl radicals may also be substituted as is apparent.

Compounds VI", IX" and X" are novel and the processes of their manufacture are also novel.

Thus according to another aspect of the invention, compounds of the formula

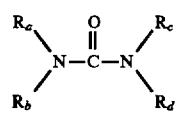

are provided wherein $R_a$ is selected from hydrogen, $R_b$ is selected from hydrogen, and a substituted phenyl radical substituted by at least one of alkoxy (for example methoxy) and cyano, and $R_c$ and $R_d$ are each selected from hydrogen, (provided $R_c$ and $R_d$ are not hydrogen when $R_a$ and $R_b$ are hydrogen) or may with the nitrogen be connected together to form a closed ring preferably containing at least a second nitrogen, (preferably being a 6-membered or 7-membered ring), the closed ring being substituted by substituted carbonyl for example R carbonyl (wherein R is selected from furyl, tetrahydrofuryl, 1,4-benzodioxan-2-yl, alkylthiooxadiazole for example methylthiooxadiazole and alkyl (for example propyl), dialkyl hydroxy alkyl ester for example, 2,2-dimethyl-2-hydroxy-ethyl ester, and alkene (for example propene).

Exemplary of such compounds are II, II', IV, IV'', IX and IX" set out below:

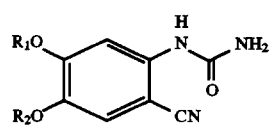

II'

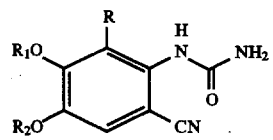

II

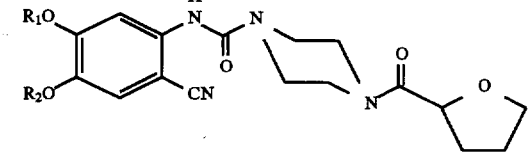

IV''

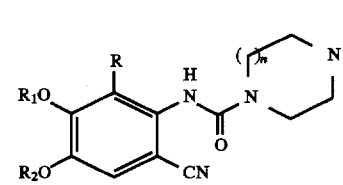

IV

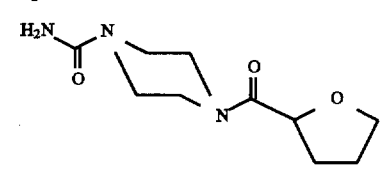

IX"

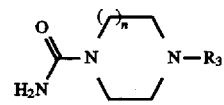

IX

According to another aspect of the invention compounds of the formula

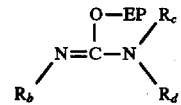

are provided, wherein:

EP is an electrophile and together with the oxygen forms a leaving group wherein —O—EP is the reaction of the urea oxygen and EP, and is leaving group substitutable by —$NH_2$ or ammonia (preferably substitutable by $NH_2$ or an amine) (preferably EP being selected from $POCl_3$, $P_2O_5$, $PCl_5$, mesyl chloride and tosyl chloride), $R_b$ is selected from hydrogen, alkyl (for example methyl) and a substituted phenyl radical substituted by at least one of alkoxy (for example methoxy) and cyano, and $R_c$ and $R_d$ are each selected from hydrogen, lower alkyl (for example methyl) a substituted phenyl radical substituted by at least one alkoxy (for example methoxy) and cyano or may with the nitrogen be connected together to form a closed ring preferably containing at least a second nitrogen, (preferably being a 6-membered or 7-membered ring), the closed ring being substituted by R-carbonyl (wherein R is selected from for example furyl, tetrahydrofuryl, 1,4-benzodioxan-2-yl, akylthiooxadiazole, for example methylthiooxadiazole, alkyl for example propyl, dialkyl hydroxy alkyl ester for example 2,2-dimethyl-2-hydroxy-ethyl ester and alkene (for example propene). Exemplary of such compounds are V, V', IIa, VIII, VIII', X and X" set out below:

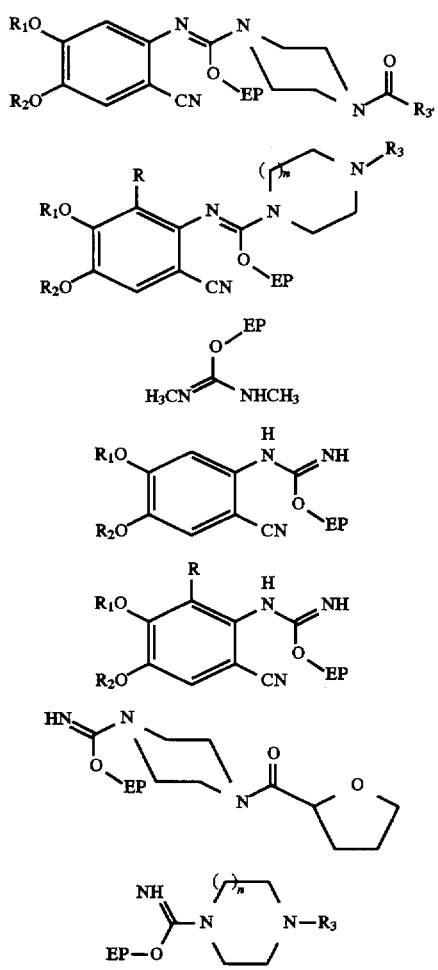

wherein —O—EP is the reaction of the urea oxygen and EP, and is a leaving group substitutable by —NH₂ or ammonia According to another aspect of the invention compounds of formula

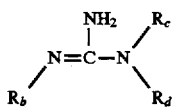

are provided wherein R_b is selected from a substituted phenyl being substituted by a radical selected from at least one of alkoxy (for example methoxy) and cyano and R_c, R_d together with the Nitrogen, form a closed ring preferably containing a second nitrogen (preferably being a 6-7 membered ring), the closed ring being substituted by furoyl, tetrahydrofuroyl, 1,4-benzodioxan-2-yl carbonyl, methylthiooxadiazole carbonyl, dialkyl hydroxy alkyl ester (for example 2, 2-dimethyl-2-hydroxy-ethyl ester), alkene (for example propene), alkoyl (for example butyroyl)

Exemplary of such compounds are compounds V, VI and VI" set out below:

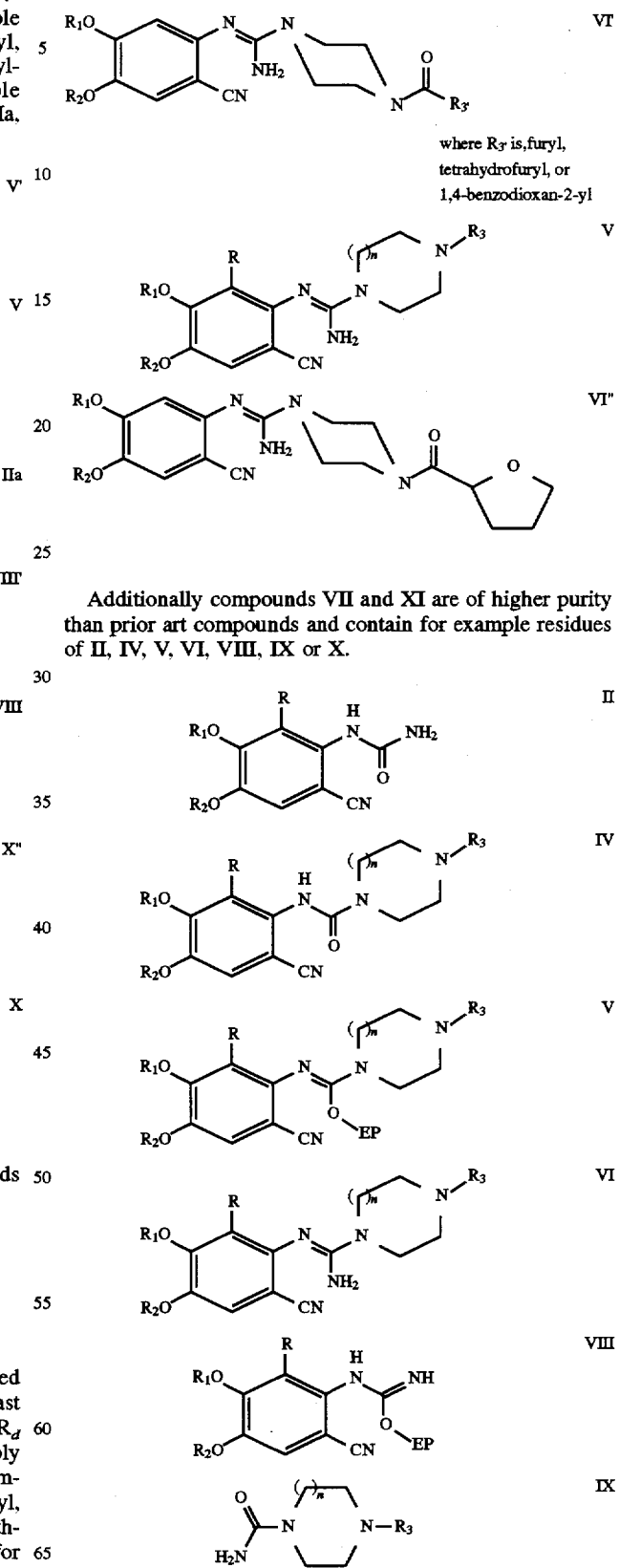

Additionally compounds VII and XI are of higher purity than prior art compounds and contain for example residues of II, IV, V, VI, VIII, IX or X.

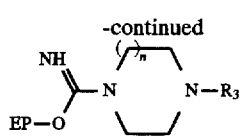

wherein the appropriate substituents are selected dependent on the medicine for example see the chart below:

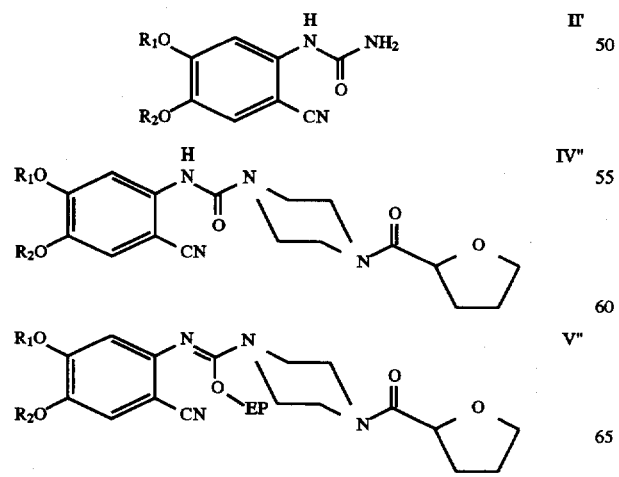

The combinations of these residues with VII and XI are also new providing a product of higher purity. Thus for example for Terazosin, the residues II', IV'', V'', VI'', VIII', IX'' and/or X'' are follows:

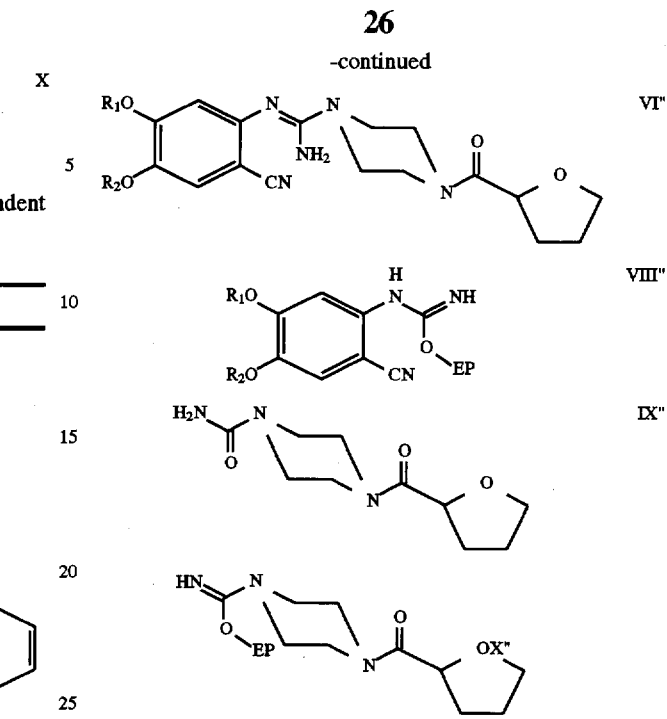

wherein —O—EP is the reaction of the urea oxygen and EP, and is a leaving group substitutable by —NH₂ or ammonia.

Where the medicine is Prazosin the residues II', IV''', V''', VI''', VIII', IX''' and/or X''' may be:

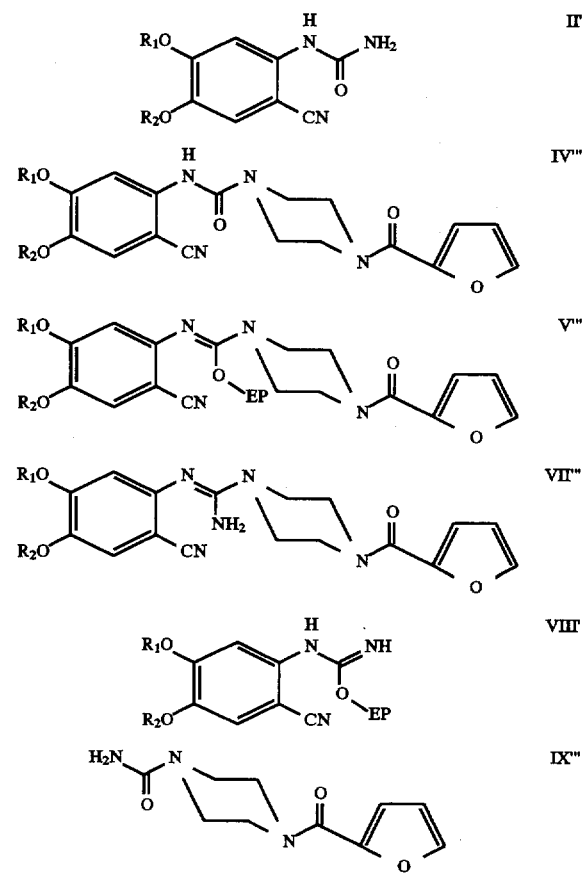

-continued (structure X''')

wherein —O—EP is the reaction of the urea oxygen and EP, and is a leaving group substitutable by —NH₂ or ammonia.

Where the medicine is doxazosin the residues II', IV', V', VI', VII', IX' and/or X' may be:

(structures II', IV', V', VI', VII', IX', X')

wherein R₃' =

(benzodioxane structure)

and wherein —O—EP is the reaction of the urea oxygen and EP, and is a leaving group substitutable by —NH₂ or ammonia.

In respect of the medicines Tiodazosin, Trimazosin, Quinasin and Bunazosin, the residues are II, IV, V, VI, VIII, IX and/or X (structure II)

-continued (structures IV, V, VI, VIII, IX, X)

wherein —O—EP is the reaction of the urea oxygen and EP, and is a leaving group substitutable by —NH₂ or ammonia wherein for the medicine:

(a) TIODAZOSIN
R is H
$R_1$ is Methyl
$R_2$ is Methyl
n is 1
and $R_3$ is (structure with N—N, O, SCH₃)

(b) TRIMAZOSIN
R is methoxy (OMe)
$R_1$ is Methyl
$R_2$ is Methyl
and $R_3$ is (ester structure with Me, Me, OH)

(c) QUINAZOSIN
R is hydrogen
$R_1$ is Methyl

R₂ is Methyl
and R₃ is

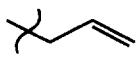

(d) BUNAZOSIN
R is hydrogen
R₁ is Methyl
R₂ is Methyl
and R₃ is

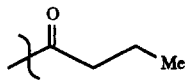

Where the medicine is Meobentine or Bethanidine, the residue includes IIa.

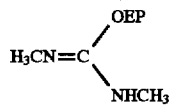

Thus the combinations of the above medicines with at least one of the associated residues is new and provides medicine having a very high purity.

The invention will now be illustrated with respect to the following exemplary methods of manufacture.

DETAILED DESCRIPTION OF PREFERRED EMBODIMENTS OF THE INVENTION

EXAMPLE 1

3,4-Dimethoxy-6-cyanoaniline-1-ylformamide (II)

3,4-Dimethoxyanthraniloniltrile (300 g, 1.69 mol) is taken in glacial acetic acid (1500 mL) and cooled to +5° C. To this solution is added a suspension of sodium cyanate (160.5 g, 2.46 mol in 750 mL of deionized water) in 100 mL portions over a thirty minute period. Acetone (6000 mL) is added and the mixture is maintained at +5° C. for an additional 30 minutes. The product is filtered and the cake is washed with acetone (2×150 mL) (293/7 grams, 79% yield).

$^1$H nmr (DMSO-d₆) d 8.19 (bs, 1H, NH); 7.48 (s, 1H, C-5); 6.98 (s, 1H, C-2); 6.12 (bs, 2H, NH₂); 3.65 (s, 3H, OCH₃); 3.60 (s, 3H, OCH₃).

EXAMPLE 2

4-(2-tetrahydrofuroyl)piperazine-1-ylformamide (IX)

4-(2-Tetrahydrofuroyl)piperazine (33.25 g, 180.7 mmol) (III) is dissolved in 165 mL water. 5N Hydrochloric acid (34.5 mL) is added and the suspension is heated to 70° C. with stirring. Sodium cyanate (13.1 g, 201.15 mmol) is added in small portion to the stirring solution and heating is continued for an additional 2 hours. The reaction mixture is concentrated under reduced pressure to yield a thick oil. Chloroform (100 mL) is added to the off and the solution is heated to reflux. The hot solution is filtered and the filtrate is dried over Na₂SO₄. The dried solution is concentrated under reduced pressure to a thick yellow oil. Ether (50 mL) is added to the oil and white crystals precipitated out. The product is filtered, washed with ether (25 mL) and dried. The product is used without further purification (33.8 g, 82.3% yield).

$^1$H nmr (CDCl₃) d 5.60 (bs, 2H, NH₂); 4.32 (t, J=7.0 Hz, 1H, CH, C-2 (tetrahydrofuroyl)); 3.80 (t, J=6.0 Hz, 2H, CH₂, C-5 (tetrahydrofuroyl)); 3.70–2.80 (m, 8H, CH₂'s (C-2, C-3, C-5, C-6 (piperazinyl))); 2.39–1.49 (m, 4H, CH₂'s (C-3, C-4 (tetrahydrofuroyl)).

EXAMPLE 3

3,4-dimethoxy-6-[4-(2-tetrahydrofuroyl)piperazine-1-ylcarbamidol] benzonitrile (IV)

3,4-Dimethoxy-6-cyanoaniline-1-ylformamide (2.75 g, 12.5 mmol) (II) and 4-(2-tetrahydrofuroyl) piperazine (2.56 g, 13.9 mmol) (III) are suspended in 25 mL dry pyridine and the mixture is refluxed for 3 hours. The solvent is then vacuum distilled to a minimum volume and then azeotroped with small portions of water. The final aqueous solution is extracted with six portions (20 mL) of ethyl acetate. The organic layer is concentrated and applied to a silica gel column (25 cm×2.5 cm). It is then eluted with ethyl acetate initially and the polarity is gradually increased with ethanol to a final solvent ratio of 80:20. Fractions containing the product (TLC: 80:20 ethylacetate:methanol, R$_f$=0.5) are combined and the solvent evaporated. The pure product is crystallized from a small volume of ethyl acetate as light yellow needles (4.27 g, 85% yield).

$^1$H nmr (CDCl₃) d 7.35 (s, 1H, ArH, C-2); 7.10 (bs, 1H, NH; 6.85 (s, 1H, ArH, C-5); 4.58 (t, J=7.0 Hz, 1H, CH, C-2 (tetrahydrofuroyl)); 3.89 (s, 3H, OCH₃); 3.80 (s, 3H, OCH₃); 4.11–3.18 (m, 10H, CH₂'s (C-2, C-3, C-5, C-6 (piperazinyl), C-5 (tetrahydrofuroyl))); 2.22–1.49 (m, 4H, CH₂'s (C-3, C-4 (tetrahydrofuroyl))).

EXAMPLE 4

3,4-dimethoxy-6-[4-(2-tetrahydrofuroyl)piperazine-1-ylcarbamido]benzonitrile(IV)

3,4-Dimethoxy-6-cyanoaniline-1-ylformamide (2.75 g, 12.5 mmol) (II) and 4-(2-tetrahydrofuroyl)piperazine (2.56 g, 13.9 mmol) (III) are suspended in 25 mL dry dimethylformamide and the mixture is refluxed for 3 hours. The solvent is then vacuum distilled to a minimum volume and then azeotroped with small portions of water. The final aqueous solution is extracted with six portions (20 mL) of ethyl acetate. The organic layer is concentrated and applied to a silica gel column (25 cm×2.5 cm). It is then eluted with ethyl acetate initially and the polarity is gradually increased with ethanol to a final solvent ratio of 80:20. Fractions containing the product (TLC: 80:20 ethylacetate:methanol, R$_f$=0.5) are combined and the solvent evaporated. The pure product is crystallized from a small volume of ethyl acetate as light yellow needles (2.85 g, 60% yield).

$^1$nmr (CDCl₃) d 7.35 (s, 1H, ArH, C-2); 7.10 (bs, 1H, NH; 6.85 (s, 1H, ArH, C-5); 4.58 (t, J=7.0 Hz, 1H, CH, C-2 (tetrahydrofuroyl)); 3.89 (s, 3H, OCH₃); 3.80 (s, 3H, OCH₃); 4.11–3.18 (m, 10H, CH₂'s (C-2, C-3, C-5, C-6 (piperazinyl), C-5 (tetrahydrofuroyl))); 2.22–1.49 (m, 4H, CH₂'s (C-3, C-4 (tetrahydrofuroyl))).

EXAMPLE 5

3,4-dimethoxy-6-[4-(2-tetrahydrofuroyl)piperazine-1-ylcarbamido]benzonitrile (IV)

(3,4-Dimethoxy-6-cyanoaniline-1-ylformamide (2.75 g, 12.5 mmol) (II) and 4-(2-tetrahydrofuroyl)piperazine (2.56 g, 13.9 mmol) (III) are suspended in 25 mL dry dichloroethane and the mixture is refluxed for 3 hours.

Water (30 mL) is added and the mixture is stirred at room temperature for 15 minutes. The layers are separated and the aqueous phase is further extracted with five portions of dichloroethane (20 mL). The organic layer is concentrated and applied to a silica gel column (25 cm×2.5 cm). It is then eluted with ethyl acetate initially and the polarity is gradually increased with ethanol to a final solvent ratio of 80:20. Fractions containing the product (TLC: 80:20 ethylacetate:methanol, $R_f$=0.5) are combined and the solvent evaporated. The pure product is crystallized from a small volume of ethyl acetate as light yellow needles (1.18 g, 25% yield).

$^1$H nmr (CDCl$_3$) d 7.35 (s, 1H, ArH, C-2); 7.10 (bs, 1H, NH; 6.85 (s, 1H, ArH, C-5); 4.58 (t, J=7.0 Hz, 1H, CH, C-2 (tetrahydrofuroyl)); 3.89 (s, 3H, OCH$_3$); 3.80 (s, 3H, OCH$_3$); 4.11–3.18 (m, 10H, CH$_2$'s (C-2, C-3, C-5, C-6 (piperazinyl), C-5 (tetrahydrofuroyl))); 2.22–1.49 (m, 4H, CH$_2$'s (C-3, C-4 (tetrahydrofuroyl))).

EXAMPLE 6

2-[4-(2-Tetrahydrofuroylpiperazine)-1-yl]-4-amino-6,7-dimethoxyquinazoline (VII)

The reaction mixture of Example 3 is cooled to 20° C. (after the three hour reflux). POCl$_3$ (2.11 g, 13.75 mmol) is added and the resulting solution is heated to 70° C. and maintained for thirty minutes. The reaction mixture is removed from the heat and allowed to cool to room temperature.[Compound V is the result]. Anhydrous, NH$_3$ gas is moderately purged through the reaction mixture and the internal temperature is allowed to rise independently to a maximum temperature (70° C.–80° C.). When the internal temperature drops below the previously attained maximum temperature, the reaction mixture is slowly heated to 100° C. (alternatively (NH$_4$)$_2$CO$_3$ can be used as a source of ammonia). The reaction mixture is cooled to 60° C. and then vacuum distilled to a minimum volume. The residual pyridine is azeotroped off with small amounts of water. Water (10 mL) and n-butanol (30 mL) are added to the aqueous solution and the mixture is heated to 60° C. The warm mixture is basified to pH-10.0 with dropwise addition of 10% NaOH. The layers are separated and the aqueous phase is further extracted with three portions (20 mL) of n-butanol. The organic extractions are combined and filtered through a bed of celite. The filtrate is dried over Na$_2$SO$_4$, concentrated under reduced pressure and applied to a silica gel column (35 cm×5 cm). It is then eluted initially with ethyl acetate and the polarity is gradually increased with ethanol to a final solvent ratio of 80:20. Fractions containing the product (TLC: 80:20 ethyl acetate:methanol, $R_f$=0.37) are combined and concentrated under reduced pressure. The pure product is crystallized from a minimum volume of ethyl acetate as white crystals (3.02 g, 67% yield).

$^1$H nmr (CDCl$_3$) d 6.98 (s, 1H, ArH, C-5); 5.52 (bs, 2H, NH$_2$); 4.82–4.50 (m, 1H, CH, C-2 (tetrahydrofuroyl)); 3.98 (s, 3H, OCH$_3$); 3.90 (s, 3H, OCH$_3$); 4.10–3.42 (m, 10H, CH$_2$'s (C-2, C-3, C-5, C-6 (piperazinyl), C-5 (tetrahydrofuroyl))); 2.39–1.75 (m, 4H, CH$_2$'s (C-3, C-4 (tetrahydrofuroyl))).

EXAMPLE 7

2-[4-(2-Tetrahydrofuroylpiperazine)-1-yl]-4-amino-6,7-dimethoxyquinazoline (VII)

The reaction mixture of Example 3 is cooled to 20° C. (after the three hour reflux). PCl$_5$ (3.90 g, 18.75 mmol) is added and the resulting solution is heated to 80° C. and maintained for thirty minutes. The reaction mixture is removed from the heat and allowed to cool to room temperature. [Compound V is the result], Anhydrous, NH$_3$ gas is moderately purged through the reaction mixture and the internal temperature is allowed to rise independently to a maximum temperature (70° C.–80° C.). When the internal temperature drops below the previously attained maximum temperature, the reaction mixture is slowly heated to 100° C. (alternatively (NH$_4$)$_2$CO$_3$ can be used as a source of ammonia). The reaction mixture is cooled to 60° C. and then vacuum distilled to a minimum volume. The residual pyridine is azeotroped off with small amounts of water. Water (10 mL) and n-butanol (30 mL) are added to the aqueous solution and the mixture is heated to 60° C. the warm mixture is basified to pH-10.0 with dropwise addition of 10% NaOH. The layers are separated and the aqueous phase is further extracted with three portions (20 mL) of n-butanol. The organic extractions are combined and filtered through a bed of celite. The filtrate is dried over Na$_2$SO$_4$, concentrated under reduced pressure and applied to a silica gel column (35 cm×5 cm). It is then eluted initially with ethyl acetate and the polarity is gradually increased with ethanol to a final solvent ratio of 80:20. Fractions containing the product (TLC: 80:20 ethyl acetate:methanol, $R_f$=0.37) are combined and concentrated under reduced pressure. The pure product is crystallized from a minimum volume of ethyl acetate as white crystals (2.78 g, 59% yield).

$^1$H nmr (CDCl$_3$) d 6.98 (s, 1H, ArH, C-5); 5.52 (bs, 2H, NH$_2$); 4.82–4.50 (m, 1H, CH, C-2 (tetrahydrofuroyl)); 3.98 (s, 3H, OCH$_3$); 3.90 (s, 3H, OCH$_3$); 4.10–3.42 (m, 10H, CH$_2$'s (C-2, C-3, C-5, C-6 (piperazinyl), C-5 (tetrahydrofuroyl))); 2.39–1.75 (m, 4H, CH$_2$'s (C-3, C-4 (tetrahydrofuroyl))).

EXAMPLE 8

2-[4-(2-Tetrahydrofuroylpiperazine-1-yl]-4-amino-6,7-dimethoxyquinazoline (VII)

The reaction mixture of Example 3 is cooled to 20° C. (after the three hour reflux). P$_2$O$_5$ (2.66 g, 18.75 mmol) is added and the resulting solution is heated to 80° C. and maintained for thirty minutes. The reaction mixture is removed from the heat and allowed to cool to room temperature.[Compound V is the result]. Anhydrous, NH$_3$ gas is moderately purged through the reaction mixture and the internal temperature is allowed to rise independently to a maximum temperature (70° C.–80° C). When the internal temperature drops below the previously attained maximum temperature, the reaction mixture is slowly heated to 100° C. (alternatively (NH$_4$)$_2$CO$_3$ can be used as a source of ammonia). The reaction mixture is cooled to 60° C. and the vacuum distilled to a minimum volume. The residual pyridine is azeotroped off with small amounts of water. Water (10 mL) and n-butanol (30 mL) are added to the aqueous solution and the mixture is heated to 60° C. The warm mixture is basified to pH-10.0 with dropwise of 10% NaOH. The layers are separated and the aqueous phase is further extracted with three portions (20 mL) of n-butanol. The organic extracts are combined and filtered through a bed of celite. The filtrate is dried over Na$_2$SO$_4$, concentrated under reduced pressure and applied to a silica gel column (35 cm×5 cm). It is then eluted initially with ethyl acetate and the polariyy is gradually increased with ethanol to a final solvent ratio of 80:20. Fractions containing the product (TLC : 80:20 ethyl acetate:methanol, $R_f$=0.37) are combined and concentrated under reduced pressure. The pure product is crystallized from a minimum volume of ethyl acetate as white crystals (0.71 g, 15% yield).

$^1$H nmr (CDCl$_3$) d 6.98 (s, 1H, ArH, C-5); 5.52 (bs, 2H, NH$_2$); 4.82–4.50 (m, 1H, CH, C-2 (tetrahydrofuroyl)); 3.98 (s, 3H, OCH$_3$); 3.90 (s, 3H, OCH$_3$); 4.10–3.42 (m, 10H, CH$_2$'s (C-2, C-3, C-5, C-6 (piperazinyl), C-5 (tetrahydrofuroyl))); 2.39–1.75 (m, 4H, CH$_2$'s (C-3, C-4 (tetrahydrofuroyl))).

EXAMPLE 9

2-[4-(2-Tetrahydrofuroylpiperazine)-1-y]l-4-amino-6,7-dimethoxyquinazoline (VII)

The reaction mixture of Example 3 is cooled to 20° C. (after the three hour reflux). P-toluenesulfonyl chloride (3.57 g, 18.75 mmol) is added and the resulting solution is heated to reflux and maintained for ninety minutes. The reaction mixture is removed from the heat and allowed to cool to room temperature.[Compound V is the result], Anhydrous NH$_3$ gas is moderately purged through the reaction mixture and the internal temperature is allowed to rise independently to a maximum temperature (70° C.–80° C). When the internal temperature drops below the previously attained maximum temperature, the reaction mixture is slowly heated to 100° C. (alternatively (NH$_4$)$_2$CO$_3$ can be used as a source of ammonia). The reaction mixture is cooled to 60° C. and the vacuum distilled to a minimum volume. The residual pyridine is azeotroped off with small amounts of water. Water (10 mL) and n-butanol (30 mL) are added to the aqueous solution and the mixture is heated to 60° C. The warm mixture is basified to pH-10.0 with dropwise addition of 10% NaOH. The layers are separated and the aqueous phase is further extracted with three portions (20 mL) of n-butanol. The organic extracts are combined and filtered through a bed of celite. The filtrate is dried over Na$_2$SO$_4$, concentrated under reduced pressure and applied to a silica gel column (35 cm×5 cm). It is then eluted initially with ethyl acetate and the polarity is gradually increased with ethanol to a final solvent ratio of 80:20. Fractions containing the product (TLC :80:20 ethyl acetate:methanol, R$_f$=0.37) are combined and concentrated under reduced pressure. The pure product is crystallized from a minimum volume of ethyl acetate as white crystals (0.23 g,5% yield).

$^1$H nmr (CDCl$_3$) d 6.98 (s, 1H, ArH, C-5); 5.52 (bs, 2H, NH$_2$); 4.82–4.50 (m, 1H, CH, C-2 (tetrahydrofuroyl)); 3.98 (s, 3H, OCH$_3$); 3.90 (s, 3H, OCH$_3$); 4.10–3.42 (m, 10H, CH$_2$'s (C-2, C-3, C-5, C-6 (piperazinyl), C-5 (tetrahydrofuroyl))); 2.39–1.75 (m, 4H, CH$_2$'s (C-3, C-4 (tetrahydrofuroyl))).

EXAMPLE 10

2-[4-(2-Tetrahydrofuroylpiperazine)-1-yl]-4-amino-6,7-dimethoxyquinazoline (VII)

Under an inert atmosphere (N$_2$) and anhydrous conditions 3,4-dimethoxy-6-cyanoanaline-1-ylformamide (2.21 g, 10 mmol) is suspended in dry pyridine (10 mL). With vigorous stirring POCl$_3$ (1.9 g, 12 mmol) is added and the solution is heated to 60° C. and maintained for fifteen minutes. 4-(2-Tetrahydrofuroyl)piperazine (2.20 g, 12 mmol) is added and the reaction mixture is brought to reflux and maintained for two hours. [Compound V is produced but not isolated]. The solvent is distilled off to a minimum volume and the residual pyridine is azeotroped off with small portions of water. Water is added to the aqueous mixture to bring the reaction volume to 30 mL. Chloroform (30 mL) is then added to the aqueous solution and with vigorous stirring the mixture is basified to pH=10 with dropwise addition of 10% NaOH. The layers are separated and the aqueous phase is further extracted with four portions (10 mL) of chloroform. The organic extracts are combined and filtered through a bed of celite. The filtrate is dried over Na$_2$SO$_4$, concentrated under reduced pressure and applied to a silica gel column (25 cm×2.5 cm). It is then eluted initially with ethyl acetate and the polarity is gradually increased with ethanol to a final solvent ratio of 80:20. Fractions containing the product (TLC: 80:20 ethyl acetate:methanol, R$_f$=0.37) are combined and concentrated under reduced pressure. The pure product is crystallized from a minimum volume of ethyl accetate as white crystals (0.77 g, 20% yield).

$^1$H nmr (CDCl$_3$) d 6.98 (s, 1H, ArH, C-5); 5.52 (bs, 2H, NH$_2$); 4.82–4.50 (m, 1H, CH, C-2 (tetrahydrofuroyl)); 3.98 (s. 3H, OCH$_3$); 3.90 (s, 3H, OCH$_3$); 4.10–3.42 (m, 10H, CH$_2$'s (C-2, C-3, C-5, C-6 (piperazinyl), C-5 (tetrahydrofuroyl))); 2.39–1.75 (m, 4H, CH$_2$'s (C-3, C-4 (tetrahydrofuroyl))).

EXAMPLE 11

2-[4-(2-Tetrahydrofuroylpiperazine)-1-yl]-4-amino-6,7-dimethoxyquinazoline (VII)

Under an inert atmosphere (N$_2$) and anhydrous conditions 3,4-dimethoxy-6-cyanoanaline-1-ylformamide (2.21 g, 10 mmol) is suspended in dry pyridine (10 mL). With vigorous stirring PCl$_5$ (2.50 g, 12 mmol) is added and the solution is heated to 60° C. and maintained for fifteen minutes. 4-(2-Tetrahydrofuroyl)piperazine (2.20 g, 12 mmol is added and the reaction mixture is brought to reflux and maintained for two hours. [Compound V was produced but not isolated]. The solvent is vacuum distilled off to a minimum volume and the residual pyridine is azeotroped off with small portions of water. Water is added to the aqueous mixture to bring the reaction volume to 30 mL. Chloroform (30 mL) is then added to the aqueous solution and with vigorous stirring the mixture is basified to pH=10 with drowise addition of 10% NaOH. The layers are separated and the aqueous phase is further extracted with four portions (10 mL) of chloroform. The organic extracts are combined and filtered through a bed of celite. The filtrate is dried over Na$_2$SO$_4$, concentrated under reduced pressure and applied to a silica gel column (25 cm×2.5 cm). It is then eluted initially with ethyl acetate and the polarity is gradually increased with ethanol to a final solvent ratio of 80:20. Fractions containing the product (TLC: 80:20 ethyl acetate:methanol, R$_f$=0.37) are combined and concentrated under reduced pressure. The pure product is crystallized from a minimum volume of ethyl acetate as white crystals (0.60 g, 16% yield).

$^1$H nmr (CDCl$_3$) d 6.98 (s, 1H, ArH, C-5); 5.52 (bs, 2H, NH$_2$); 4.82–4.50 (m, 1H, CH, C-2 (tetrahydrofuroyl)); 3.98 (s, 3H, OCH$_3$); 3.90 (s, 3H, OCH$_3$); 4.10–3.42 (m, 10H, CH$_2$'s (C-2, C-3, C-5, C-6 (piperazinyl), C-5 (tetrahydrofuroyl))); 2.39–1.75 (m, 4H, CH$_2$'s (C-3, C-4 (tetrahydrofuroyl))).

EXAMPLE 12

2-[4-(2-Tetrahydrofuroylpiperazine)-1-yl]-4-amino-6,7-dimethoxyquinazoline (VII)

3,4-Dimethoxy-6-cyanoanaline-1-ylformamide (2.21 g, 10 mmol) is suspended in dry pyridine (10 mL) and with stirring p-toluenesulfonyl chloride (2.5 g, 13 mmol) is added portionwise. The reaction mixture is heated on a water bath (60° C.) until complete dissolution is achieved 4-(2-Tetrahydrofuroyl)piperazine (2.20 g, 12 mmol) is added and the mixture is brought to reflux and maintained for two hours. The solvent is vacuum distilled off to a minimum volume and the residual pyridine is azeotroped off with small portions of water. Water is added to the aqueous mixture to bring the reaction volume to 30 mL. Chloroform (30 mL) is then added to the aqueous solution and with vigorous stirring the mixture is basified to pH=10 with dropwise addition of 10% NaOH. The layers are separated and the aqueous phase is further extracted with four portions (10 mL) of chloroform. The organic extracts are combined and filtered through a bed of celite. The filtrate is dried over $Na_2SO_4$, concentrated under reduced pressure and applied to a silica gel column (25 cm×2.5 cm). It is then eluted initially with ethyl acetate and the polarity is gradually increased with ethanol to a final solvent ratio of 80:20. Fractions containing the product (TIC: 80:20 ethyl acetate:methanol, $R_f$=0.37) are combined and concentrated under reduced pressure. The pure product is crystallized from a minimum volume of ethyl acetate as white crystals (0.53 g, 14% yield).

$^1$H nmr (CDCl$_3$) d 6.98 (s, 1H, ArH, C-5); 5.52 (bs, 2H, NH$_2$); 4.82–4.50 (m, 1H, CH, C-2 (tetrahydrofuroyl)); 3.98 (s, 3H, OCH$_3$); 3.90 (s, 3H, OCH$_3$); 4.10–3.42 (m, 10H, CH$_2$'s (C-2, C-3, C-5, C-6 (piperazinyl), C-5 (tetrahydrofuroyl))); 2.39–1.75 (m, 4H, CH$_2$'s (C-3, C-4 (tetrahydrofuroyl))).

EXAMPLE 13

2-[4-(2-Tetrahydrofuroylpiperazine)-1-yl]-4-amino-6,7-dimethoxyquinazoline (VII)

3,4-dimethoxy-6-cyanoanaline-1-ylformamide (2.21 g, 10 mmol) is suspended in dry dichloroethane (10 mL) and triethylamine (2.0 g, 20 mmol) is added and the suspension is stirred for 10 minutes. P-toluenesulfonyl chloride (2.5 g, 13 mmol) is added portionwise and the reaction mixture is heated to reflux and maintained for one hour. The mixture is allowed to cool to room temperature and 4-(2-Tetrahydrofuroyl)piperazine (2.20 g, 12 mmol) is added and the mixture is brought to reflux and maintained for two hours. Water (30 mL) is added and with vigorous stirring the mixture is basified to pH:10 with dropwise addition of 10% NaOH. The layers are separated and the aqueous phase is further extracted with four portions (10 mL) of dichloroethane. The organic extracts are combined and filtered through a bed of celite. The filtrate is dried over Na$_2$SO$_4$, concentrated under reduced pressure and applied to a silica gel column (25 cm×2.5 cm). It is then eluted initially with ethyl acetate and the polarity is gradually increased with ethanol to a final solvent ratio of 80:20. Fractions containing the product (TLC: 80:20 ethyl acetate:methanol, R$_f$:0.37) are combined and concentrated under reduced pressure. The pure product is crystallized from a minimum volume of ethyl acetate as white crystals (0.38 g, 10% yield).

$^1$H nmr (CDCl$_3$) d 6.98 (s, 1H, ArH, C-5); 5.52 (bs, 2H, NH$_2$); 4.82–4.50 (m, 1H, CH, C-2 (tetrahydrofuroyl)); 3.98 (s, 3H, OCH$_3$); 3.90 (s, 3H, OCH$_3$); 4.10–3.42 (m, 10H, CH,$_2$'s (C-2, C-3, C-5, C-6 (piperazinyl), C-5 (tetrahydrofuroyl))); 2.39–1.75 (m, 4H, CH$_2$'s (C-3, C-4 (tetrahydrofuroyl))).

EXAMPLE 14

2-[4-(2-Tetrahydrofuroylpiperazine)-1yl]-4-amino-6,7-dimethoxyquinazoline (VII)

4-(2-Tetrahyrofuroyl)piperazine-1-yl-formamide (2.27 g, 10 mmol) is suspended in dichloroethane (15 mL) and heated until total dissolution is achieved. Triethylamine (2.0 g, 20 mmol) is added and the solution is stirred for 5 minutes. P-toluenesulfonyl chloride (3.92 g, 20 mmol) is added and the reaction mixture is heated to reflux and maintained for 3 hours. Compound X is produced. 3,4-Dimethoxyanthralinonitrile (1.78 g, 10 mmol) is added and reflux is continued for an additional 24 hours. [Compound VI is the result]. Water (30 mL) is added and with vigorous stirring the mixture is basified to pH=10 with dropwise addition of 10% NaOH. The layers are separated and the aqueous phase is further extracted with four portions (10 mL) of dichloroethane. The organic extracts are combined and filtered through a bed of celite. The filtrate is dried over Na$_2$SO$_4$, concentrated under reduced pressure and applied to a silica gel column (25 cm×2.5 cm). It is then eluted initially with ethyl acetate and the polarity is gradually increased with ethanol to a final solvent ratio of 80:20. Fractions containing the product (TLC: 80:20 ethyl acetate:methanol, R$_f$=0.37) are combined and concentrated under reduced pressure. The pure product is crystallized from a minimum volume of ethyl acetate as white crystals (0.76 g, 20% yield).

$^1$H nmr (CDCl$_3$) d 6.98 (s, 1H, ArH, C-5); 5.52 (bs, 2H, NH$_2$); 4.82–4.50 (m, 1H, CH, C-2 (tetrahydrofuroyl)), 3.98 (s, 3H, OCH$_3$); 3.90 (s, 3H, OCH$_3$); 4.10–3.42 (m, 10H, CH$_2$'s (C-2, C-3, C-5, C-6 (piperazinyl), C-5 (tetrahydrofuroyl))); 2.39–1.75 (m, 4H, CH$_2$'s (C-3, C-4 (tetrahydrofuroyl))).

EXAMPLE 15

2-[4-(2-Tetrahydrofuroylpiperazine)- 1-yl]-4-amino-6,7-dimethoxyquinazoline (VII)

A mixture of 3,4-dimethoxyanthranilonitrile (7.91 g, 44.5 mmol), 4-(2-Tetrahyrofuroyl)piperazine-1-yl-formamide (10.1 g, 44.5 mmol) and P$_2$O$_5$ (32.0 g, 225 mmol) in dry pyridine (50 mL) is refluxed with stirring for 2.5 hours. The reaction mixture is then allowed to cool to room temperature over a 1 hour period and then poured into a vessel containing sodium bicarbonate (60 g). The reaction vessel is then washed with four portions of water (50 mL) which are combined with bicarbonate mixture. The mixture is stirred for 30 minutes and filtered. The filtrate is then extracted with four portions of chloroform (100 ml). The organic layers are combined, dried over Na$_2$SO$_4$ and concentrated under reduced pressure. The orange oil obtained is applied to a silica gel column (25 cm×2.5 cm) and is eluted initially with ethyl acetate and the polarity is gradually increased with ethanol to a final solvent ratio of 80:20. Fractions containing the product (TLC: 80:20 ethyl acetate: methanol, R$_f$=0.37) are combined and concentrated under reduced pressure. The pure product is crystallized from a minimum volume of ethyl acetate as white crystals (2.05 g, 12% yield).

$^1$H nmr (CDCl$_3$) d 6.98 (s, 1H, ArH, C-5); 5.52 (bs, 2H, NH$_2$); 4.82–4.50 (m, 1H, CH, C-2 (tetrahydrofuroyl)); 3.98 (s, 3H, OCH$_3$); 3.90 (s, 3H, OCH$_3$); 4.10–3.42 (m, 10H, CH$_2$'s (C-2, C-3, C-5, C-6 (piperazinyl), C-5 (tetrahydrofuroyl))); 2.39–1.75 (m, 4H, CH$_2$'s (C-3, C-4 (tetrahydrofuroyl))).

EXAMPLE 16

2-[4-(2-Tetrahydrofuroylpiperazine)-1-yl]-4-amino-6,7-dimethoxyquinazoline (VII)

A mixture of 3,4-dimethoxy-6-cyanoaniline-1-ylformamide (10.6 g, 48 mmol) (II), 4-(2-tetrahydrofuroyl) piperazine (8.8 g, 48 mmol) (III) and P$_2$O$_5$ (36 g, 250 mmol)

in dry pyridine (100 mL) is refluxed with stirring for 4 hours. The reaction mixture is then allowed to cool to room temperature over a 1 hour period and then poured into a vessel containing sodium bicarbonate (60 g). The reaction vessel is then washed with four portions of water (50 mL) which are combined with bicarbonate mixture. The mixture is stirred for 30 minutes and filtered. The filtrate is then extracted with four portions of chloroform (100 ml). The organic layers are combined, dried over $Na_2SO_4$ and concentrated under reduced pressure. The orange off obtained is applied to a silica gel column (25 cm×2.5 cm) and is eluted initially with ethyl acetate and the polarity is gradually increased with ethanol to a final solvent ratio of 80:20. Fractions containing the product (TLC: 80:20 ethyl acetate: methanol, $R_f$:0.37) are combined and concentrated under reduced pressure. The pure product is crystallized from a minimum volume of ethyl acetate as white crystals (1.85 g, 10% yield).

$^1$H nmr (CDCl$_3$) d 6.98 (s. 1H, ArH, C-5); 5.52 (bs, 2H, NH$_2$); 4.82–4.50 (m, 1H, CH, C-2 (tetrahydrofuroyl)); 3.98 (s, 3H, OCH$_3$); 3.90 (s, 3H, OCH$_3$); 4.10–3.42 (m, 10H, CH$_2$'s (C-2, C-3, C-5, C-6 (piperazinyl), C-5 (tetrahydrofuroyl))); 2.39–1.75 (m, 4H, CH$_2$'s (C-3, C-4 (tetrahydrofuroyl))).

EXAMPLE 17

2-[4-(2-Tetrahydrofuroylpiperazine)-1-yl]-4-amino-6,7-dimethoxyquinazoline (VII)

4-(2-Tetrahyrofuroyl)piperazine-1-yl-formamide (2.27 g, 10 mmol) is suspended in dichloroethane (15 mL) and heated until total dissolution is achieved. Triethylamine (2.0 g, 20 mmol is added and the solution is stirred for 5 minutes. Methanesulfonyl chloride (2.29 g, 20 mmol) is added and the reaction mixture is heated to reflux and maintained for 1 hour. 3,4-Dimethoxyanthranilonitrile (1.78 g, 10 mmol is added and reflux is continued for an additional 24 hours. Water (30 mL) is added and with vigorous stirring the mixture is basified to pH:10 with dropwise addition of 10% NaOH. The layers are separated and the aqueous phase is further extracted with four portions (10 mL) of dichloroethane. The organic extractions are combined and filtered through a bed of celite. The filtrate is dried over Na$_2$SO$_4$, concentrated under reduced pressure and applied to a silica gel column (25 cm×2.5 cm). It is then eluted initially with ethyl acetate and the polarity is gradually increased with ethanol to a final solvent ratio of 80:20. Fractions containing the product (TLC: 80:20 ethyl acetate:methanol, R$_f$=0.37) are combined and concentrated under reduced pressure. The pure product is crystallized from a minimum volume of ethyl acetate as white crystals (0.83 g, 22% yield).

$^1$H nmr (CDCl$_3$) d 6.98 (s, 1H, ArH, C-5); 5.52 (bs, 2H, NH$_2$); 4.82–4.50 (m, 1H, CH, C-2 (tetrahydrofuroyl)); 3.98 (s, 3H, OCH$_3$); 3.90 (s, 3H, OCH$_3$); 4.10–3.42 (m, 10H, CH$_2$'s (C-2, C-3, C-5, C-6 (piperazinyl), C-5 (tetrahydrofuroyl))); 2.39–1.75 (m, 4H, CH$_2$'s (C-3, C-4 (tetrahydrofuroyl))).

EXAMPLE 18

2-[4-(2-Tetrahydrofuroylpiperazine)-1-yl]-4-amino-6,7-dimethoxyquinazoline (VII)

4-(2-Tetrahyrofuroyl)piperazine-1-yl-formamide (2.27 g, 10 mmol) is suspended in dry pyridine (10 mL) and with stirring POCl$_3$ (1.8 g, 12 mmol) is added and the reaction mixture is stirred for an additional ten minutes. 3,4-Dimethoxyanthranilonitrile (1.78 g, 10 mmol) is added and the mixture is brought to reflux and maintained for three hours. The solvent is vacuum distilled off to a minimum volume and the residual pyridine is azeotroped off with small portions of water. Water is added to the aqueous mixture to bring the reaction volume to 30 mL. Chloroform (30 mL) is then added to the aqueous solution and with vigorous stirring the mixture is basified to pH=10 with dropwise addition of 10% NaOH. The layers are separated and the aqueous phase is further extracted with four portions (10 mL) of chloroform. The organic extracts are combined and filtered through a bed of celite. The filtrate is dried over Na$_2$SO$_4$, concentrated under reduced pressure and applied to a silica gel column (25 cm×2.5 cm). It is then eluted initially with ethyl acetate and the polarity is gradually increased with ethanol to a final solvent ratio of 80:20. Fractions containing the product (TLC : 80:20 ethyl acetate:methanol, R$_f$=0.37) are combined and concentrated under reduced pressure. The pure product is crystallized from a minimum volume of ethyl acetate as white crystals (0.26 g, 7% yield).

$^1$H nmr (CDCl$_3$) d 6.98 (s, 1H, ArH, C-5); 5.52 (bs, 2H, NH$_2$); 4.82–4.50 (m, 1H, CH, C-2 (tetrahydrofuroyl)); 3.98 (s, 3H, OCH$_3$); 3.90 (s, 3H, OCH$_3$); 4.10–3.42 (m, 10H, CH$_2$'s (C-2, C-3, C-5, C-6 (piperazinyl), C-5 (tetrahydrofuroyl))); 2.39–1.75 (m, 4H, CH$_2$'s (C-3, C-4 (tetrahydrofuroyl))).

EXAMPLE 19

2-[4-(2-Tetrahydrofuroylpiperazine-1-yl]-4- amino-6,7-dimethoxyquinazoline (VII)

4-(2-Tetrahyrofuroyl)piperazine-1-yl-formamide (2.27 g, 10 mmol) is suspended in dichloroethane (15 mL) and with stirring POCl$_3$ (1.8 g, 12 mmol) is added and the reaction mixture is stirred for an additional ten minutes. 3,4-Dimethoxyanthranilonitrile (1.78 g. 10 mmol) is added and the mixture is brought to reflux and maintained for 24 hours. Water (30 mL) is added and with vigorous stirring the mixture is basified to pH:10 with dropwise addition of 10% NaOH. The layers are separated and the aqueous phase is further extracted with four portions (10 mL) of dichloroethane. The organic extracts are combined and filtered through a bed of celite. The filtrate is dried over Na$_2$SO$_4$, concentrated under reduced pressure and applied to a silica gel column (25 cm×2.5 cm). It is then eluted initially with ethyl acetate and the polarity is gradually increased with ethanol to a final solvent ratio of 80:20. Fractions containing the product (TLC: 80:20 ethyl acetate:methanol, R$_f$=0.45) are combined and concentrated under reduced pressure. The pure product is crystallized from a minimum volume of ethyl acetate as white crystals (0.30 g, 8% yield);

$^1$H nmr (CDCl$_3$) d 6.98 (s, 1H, ArH, C-5); 5.52 (bs, 2H, NH$_2$); 4.82–4.50 (m, 1H, CH, C-2 (tetrahydrofuroyl)); 3.98 (s, 3H, OCH$_3$); 3.90 (s, 3H, OCH$_3$); 4.10–3.42 (m, 10H, CH$_2$'s (C-2, C-3, C-5, C-6 (piperazinyl), C-5 (tetrahydrofuroyl))); 2.39–1.75 (m, 4H, CH$_2$'s (C-3, C-4 (tetrahydrofuroyl))).

EXAMPLE 20

2-[4-(2-Tetrahydrofuroylpiperazine)-1-yl]-4-amino-6,7-dimethoxyquinazoline (VII)

4-(2-Tetrahyrofuroyl)piperazine-1-yl-formamide (2.27 g, 10 mmol) is suspended in dichloroethane (15 mL) and with stirring, triethylamine (1.2 g, 12 mmol) is added and the reaction mixture is stirred for 15 minutes. POCl$_3$ (1.8 g. 12 mmol) is added and the mixture is heated to reflux and maintained for ten minutes. The reaction is cooled to room temperature and 3,4-dimethoxyanthranilonitrile (1.78 g, 10 mmol) is added and the mixture is brought to reflux and maintained for 24 hours. Water (30 mL) is added and with vigorous stirring the mixture is basified to pH=10 with dropwise addition of 10% NaOH. The layers are separated and the aqueous phase is further extracted with four portions (10 mL) of dichloroethane. The organic extracts are combined and filtered through a bed of celite. The filtrate is dried over $Na_2SO_4$, concentrated under reduced pressure and applied to a silica gel column (25 cm×2.5 cm). It is then eluted initially with ethyl acetate and the polarity is gradually increased with ethanol to a final solvent ratio of 80:20. Fractions containing the product (TLC : 80:20 ethyl acetate:methanol, $R_f$=0.37) are combined and concontrated under reduced pressure. The pure product is crystallized from a minimum volume of ethyl acetate as white crystals (0.35 g, 9.2% yield).

$^1$H nmr (CDCl$_3$) d 6.98 (s, 1H, ArH, C-5); 5.52 (bs, 2H, NH$_2$); 4.82–4.50 (m, 1H, CH, C-2 (tetrahydrofuroyl)); 3.98 (s, 3H, OCH$_3$); 3.90 (s, 3H, OCH$_3$); 4.10–3.42 (m, 10H, CH$_2$'s (C-2, C-3, C-5, C-6 (piperazinyl), C-5 (tetrahydrofuroyl))); 2.39–1.75 (m, 4H, CH$_2$'s (C-3, C-4 (tetrahydrofuroyl))).

EXAMPLE 21

2-[4-(2-Tetrahydrofuroylpiperazine)-1-yl]-4-amino-6,7-dimethoxyquinazoline Hydrochloride Dihydrate (XI)

Terazosin free base (VII, 3.87 g, 10 mmol) was suspended in 20 mL hot isopropanol and concentrated hydrochloric acid (5 mL) was added. A solution was obtained which was concentrated to dryness under reduced pressure. Isopropanol (20 mL) was then added and the resulting suspension was brought to reflux and then cooled to room temperature. The slurry was filtered and washed with a small volume of isopropanol. Yield 4.1 g (90% yield), mp 271–273.

As many changes can be made to the examples without departing from the scope of the invention, it is intended that all material contained herein be interpreted as illustrative of the invention and not in a limiting sense.

The embodiments of the invention in which an exclusive property or privilege is claimed are as follows:

1. The process of reacting compound (VIII) of the formula

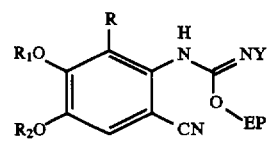

VIII to give compound (VI) of the formula

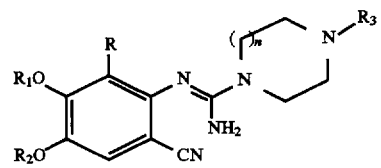

VI wherein Y is (i) hydrogen or wherein NY is (ii) a compound of the formula

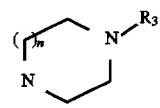

and when Y is H, compound (VIII) is reacted with compound (III) of the formula

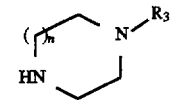

III and when NY is (ii), compound (VIII) is reacted with NH$_3$.

2. The process of claim 1 wherein NY is (ii) and the reaction comprises reacting:

intermediate (V) of the formula

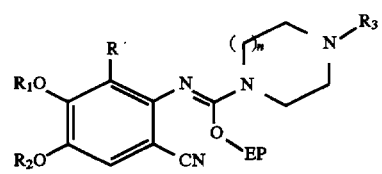

V in the presence of NH$_3$ to give compound (VI) of the formula

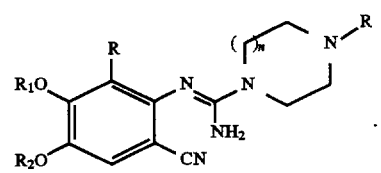

VI

3. The process of claim 2 further comprising closing a ring in:

compound (VI) of the formula

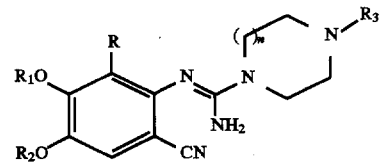

VI to give compound (VII) of the formula

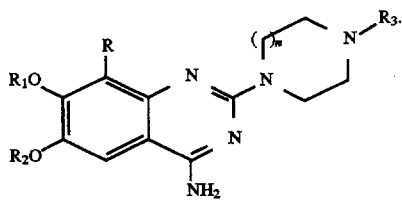

VII

4. The process of claim 2 or 3 further comprising reacting compound (VI) or compound (VII) thereof to produce a medicine selected from the group consisting of Terazosin, Prazosin, Doxazosin, Tiodazosin, Trimazosin, Quinazosin or Bunazosin.

5. A process comprising reacting:

compound (V') of the formula

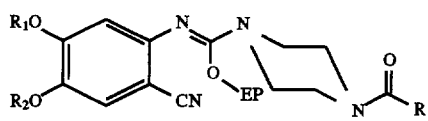

in the presence of NH$_3$ to give compound (VI') of the formula

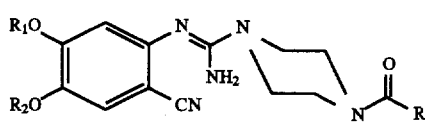

wherein O—EP is a leaving group substitutable by —NH$_2$ or an amine and wherein EP is selected from the group consisting of POCL$_3$, PCl$_5$, P$_2$O$_5$, TsCl and wherein R is tetrahydrofuryl, furyl or 1-4-benzodioxan-2-yl.

6. The process of claim 5 wherein R is tetrahydrofuryl further comprising reacting compound (VI') to produce Terazosin or a form thereof.

7. The process of claim 5 wherein R is furyl further comprising reacting compound (VI') to produce Prazosin.

8. The process of claim 5 wherein R is 1,4-benzodioxan-2-yl, further comprising reacting compound (VI') to produce Doxazosin.

9. The process of claim 5 where R is tetrahydrofuryl further comprising closing the ring in:

compound (VI") of the formula

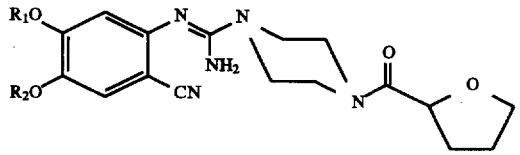

to give compound (VII") of the formula

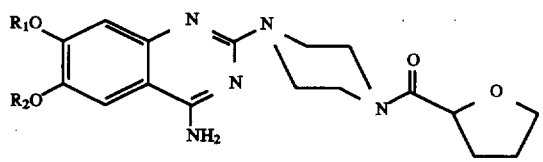

10. The process of claim 9 further comprising reacting compound (VII") to produce Terazosin hydrochloride dihydrate.

11. A process comprising closing a ring in:
compound (VI') of the formula

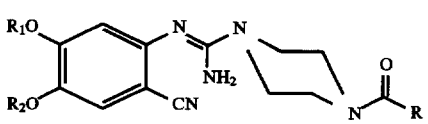

to give compound (VII') of the formula

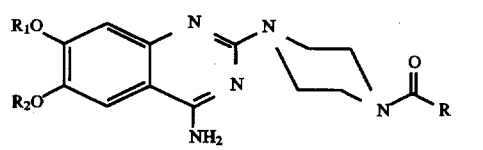

wherein R is selected from furyl and 1,4-benzodioxan-2-yl.

12. The process of claim 11 wherein R is furyl further comprising reacting compound (VII') to produce Prazosin.

13. The process of claim 11 wherein R is 1,4-benzodioxan-2-yl, further comprising reacting compound (VII') to produce Doxazosin.

14. The process of claim 1 wherein Y is H and the reaction comprises reacting:

intermediate (VIII) of the formula

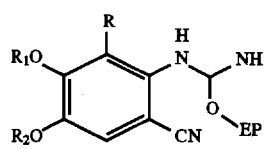

to give compound (VI) of the formula

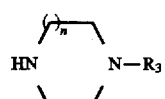

to give compound (VI) of the formula

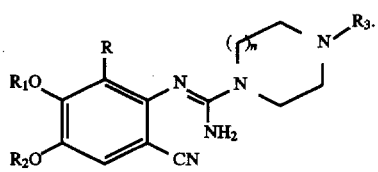

15. The process of claim 14 further comprising closing a ring in:

compound (VI) of the formula

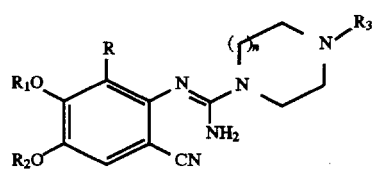

to give compound (VII) of the formula

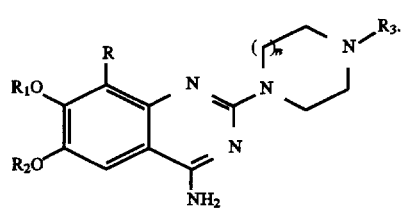

16. The process of claim 14 or 15 further comprising reacting compound (VI) or compound (VII) thereof to produce a medicine selected from Terazosin, Prazosin, Doxazosin, Tiodazosin, Trimazosin, Quinazosin or Bunazosin.

17. The process of claim 15 further comprising reacting:
compound (II') of the formula

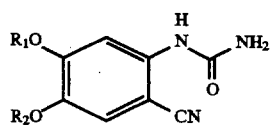

in the presence of EP to give the intermediate (VIII) of the formula

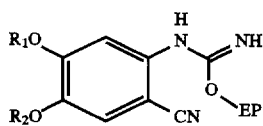

VIII' wherein O—EP is a leaving group substitutable by —NH₂ or an amine.

18. The process of claim 17 further comprising reacting compound (VIII') to produce a compound selected from Terazosin, Terazosin hydrochloride dihydrate, Prazosin or Doxazosin.

19. The process of claim 14 comprising:

reacting compound (VIII') of the formula

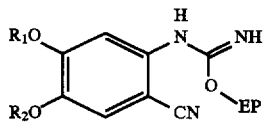

VIII' with compound (III") of the formula

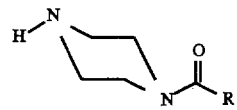

III"

to give compound (VI") of the formula

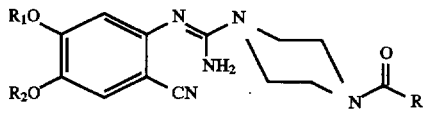

VI"

wherein O—EP is a leaving group substitutable by —NH₂ and where $R_1$ and $R_2$ are methyl and R is selected from furyl, tetrahydrofuryl and 1,4-benzodioxan-2-yl.

20. The process of claim 19 further comprising reacting compound (VI") to produce a product selected from Terazosin, Terazosin hydrochloride dihydrate, Prazosin or Doxazosin.

* * * * *